(12) United States Patent
Kim

(10) Patent No.: US 9,839,583 B2
(45) Date of Patent: Dec. 12, 2017

(54) APPARATUS FOR DISPENSING TABLETS AND METHOD FOR CONTROLLING THE SAME

(71) Applicant: JVM CO., LTD., Daegu (KR)

(72) Inventor: Jun Ho Kim, Daegu (KR)

(73) Assignee: JVM CO., LTD., Daegu (KR)

( * ) Notice: Subject to any disclaimer, the term of this patent is extended or adjusted under 35 U.S.C. 154(b) by 0 days.

(21) Appl. No.: 14/432,094

(22) PCT Filed: Sep. 12, 2013

(86) PCT No.: PCT/KR2013/008247
§ 371 (c)(1),
(2) Date: Mar. 27, 2015

(87) PCT Pub. No.: WO2014/051281
PCT Pub. Date: Apr. 3, 2014

(65) Prior Publication Data
US 2015/0290084 A1 Oct. 15, 2015

(30) Foreign Application Priority Data

Sep. 27, 2012 (KR) .................. 10-2012-0107883
Sep. 27, 2012 (KR) .................. 10-2012-0107884
Sep. 27, 2012 (KR) .................. 10-2012-0108141

(51) Int. Cl.
| | | |
|---|---|---|
| B65G 47/14 | (2006.01) | |
| B65G 59/00 | (2006.01) | |
| G07F 11/00 | (2006.01) | |
| B65B 5/04 | (2006.01) | |
| A61J 7/00 | (2006.01) | |
| B65B 5/00 | (2006.01) | |
| B65B 55/24 | (2006.01) | |
| B65B 5/10 | (2006.01) | |
| G06F 19/00 | (2011.01) | |
| B65B 57/10 | (2006.01) | |

(52) U.S. Cl.
CPC .............. *A61J 7/0069* (2013.01); *B65B 5/00* (2013.01); *B65B 5/103* (2013.01); *B65B 55/24* (2013.01); *B65B 57/10* (2013.01); *G06F 19/3462* (2013.01)

(58) Field of Classification Search
CPC .......... A61J 7/0069; B65B 5/00; B65B 5/103; B65B 55/24; B65B 57/10; G06F 19/00; G06F 19/3462; G06Q 50/22
USPC ............ 221/1, 312, 312 B; 53/246, 51, 474; 700/243
See application file for complete search history.

(56) References Cited

U.S. PATENT DOCUMENTS 5,709,063 A 1/1998 Yuyama et al.
7,438,201 B2 * 10/2008 Kim .................. B65B 5/103
221/200

(Continued)

FOREIGN PATENT DOCUMENTS

JP 2000-168702 A 6/2000
KR 10-0243851 B1 3/2000
(Continued)

*Primary Examiner* — Rakesh Kumar
(74) *Attorney, Agent, or Firm* — Birch, Stewart, Kolasch & Birch, LLP

(57) ABSTRACT

An apparatus for dispensing tablets according to an embodiment of the present invention includes a main body including a plurality of tablet input parts to collect the inputted tablets in a tray disposed therein; and at least one input sensor disposed in the main body to sense whether the tablets are inputted.

6 Claims, 29 Drawing Sheets

(56) References Cited

U.S. PATENT DOCUMENTS

| | | | | |
|---|---|---|---|---|
| 7,587,878 | B2* | 9/2009 | Kim | A61J 7/0069 53/246 |
| 7,848,846 | B2* | 12/2010 | Uema | G07F 11/62 221/119 |
| 8,914,146 | B2* | 12/2014 | Carson | B65B 57/16 700/213 |
| 9,211,233 | B2* | 12/2015 | Shavelsky | A61J 7/04 |
| 9,355,222 | B2* | 5/2016 | Chudy | G06F 19/3462 |
| 2006/0273106 | A1 | 12/2006 | Kim | |
| 2009/0188937 | A1* | 7/2009 | Kim | A61J 7/0069 221/312 B |
| 2010/0018986 | A1* | 1/2010 | Kodama | B65B 5/103 221/8 |
| 2012/0006708 | A1* | 1/2012 | Mazur | A61J 7/0481 206/438 |
| 2013/0026174 | A1* | 1/2013 | Yuyama | G07F 11/00 221/2 |
| 2015/0290084 | A1* | 10/2015 | Kim | A61J 7/0069 221/1 |
| 2016/0000657 | A1* | 1/2016 | Dickie | A61J 7/0481 206/534 |
| 2016/0074283 | A1* | 3/2016 | Aggarwal | A61J 7/04 206/534 |
| 2017/0017775 | A1* | 1/2017 | Dent | G06F 19/3462 |

FOREIGN PATENT DOCUMENTS

| | | |
|---|---|---|
| KR | 20-0338658 Y1 | 1/2004 |
| KR | 10-2004-0055646 A | 6/2004 |
| KR | 10-0591519 B1 | 6/2006 |
| KR | 10-2009-0018533 A | 2/2009 |
| KR | 10-2009-0020158 A | 2/2009 |
| KR | 10-2009-0055578 A | 6/2009 |
| KR | 10-2009-0081992 A | 7/2009 |
| KR | 10-1122361 B1 | 3/2012 |

* cited by examiner

<First Day>

(A)

|   | Morning | Lunch | Dinner |
|---|---------|-------|--------|
| A | 1 | 0 | 0 |
| B | 1 | 0 | 2 |
| C | 2 | 2 | 2 |
| ⋮ | ⋮ | ⋮ | ⋮ |

<Second Day>

(B)

|   | Morning | Lunch | Dinner |
|---|---------|-------|--------|
| A | 1 | 0 | 0 |
| B | 1 | 0 | 1 |
| C | 1 | 1 | 1 |
| D | 1 | 1 | 1 |
| ⋮ | ⋮ | ⋮ | ⋮ |

<Third Day>

(C)

|   | Morning | Lunch | Dinner |
|---|---------|-------|--------|
| A | 1 | 0 | 0 |
| B | 0 | 0 | 0 |
| C | 0 | 0 | 0 |
| D | 1 | 1 | 1 |
| ⋮ | ⋮ | ⋮ | ⋮ |

<Selection of Tablet A> fig. 28
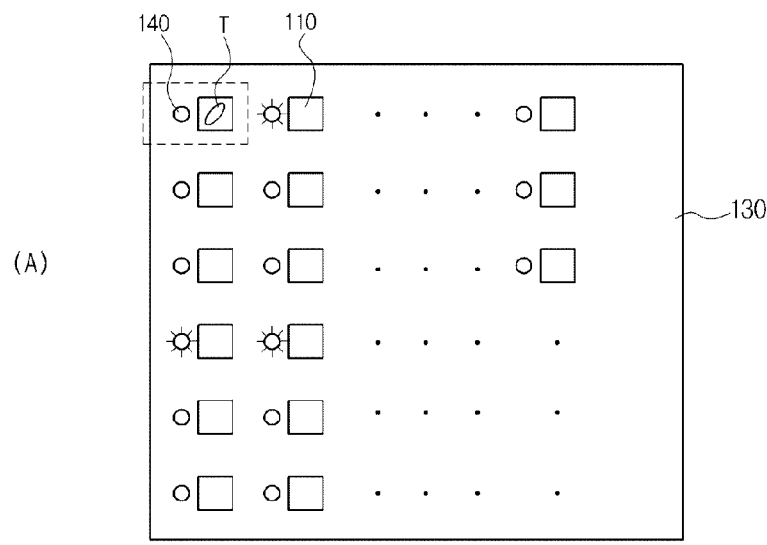
(A)
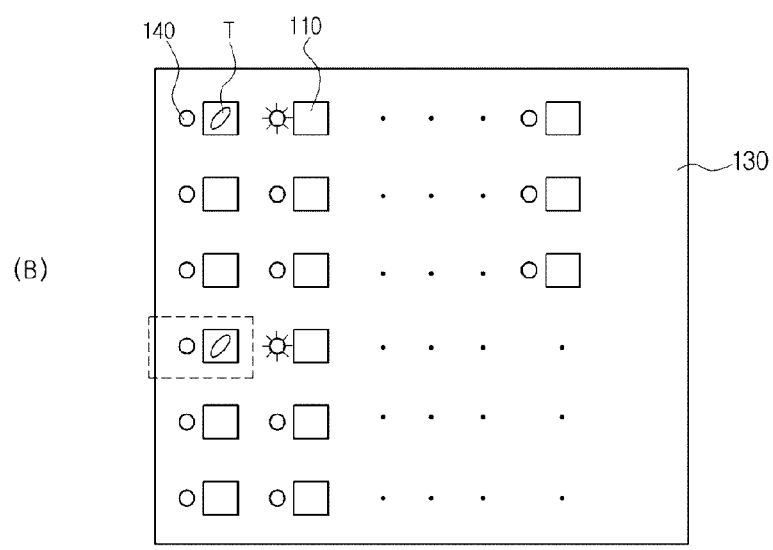
(B)

fig. 29
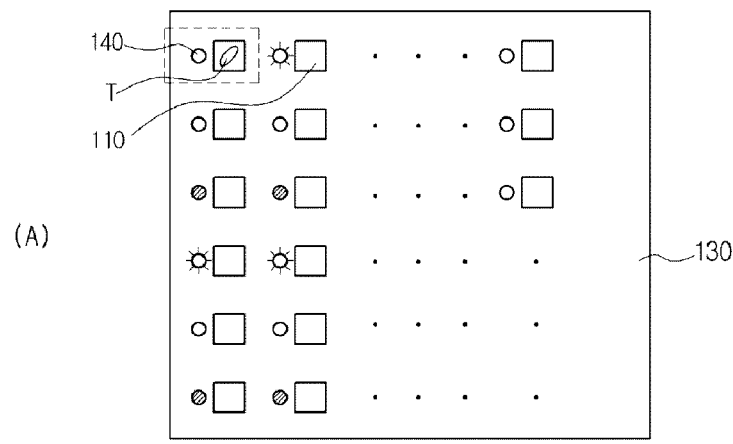
(A)
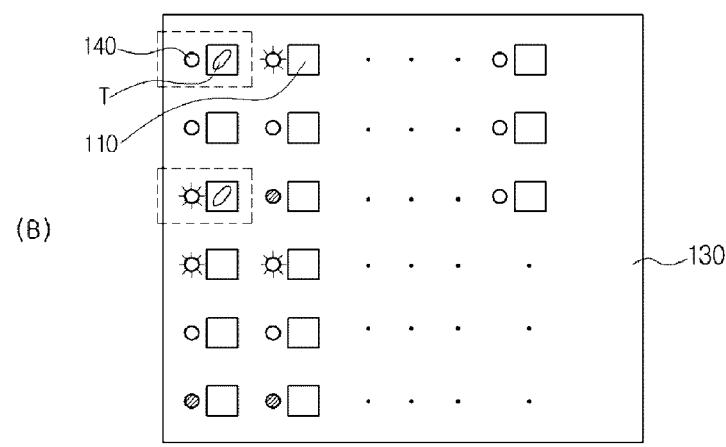
(B)
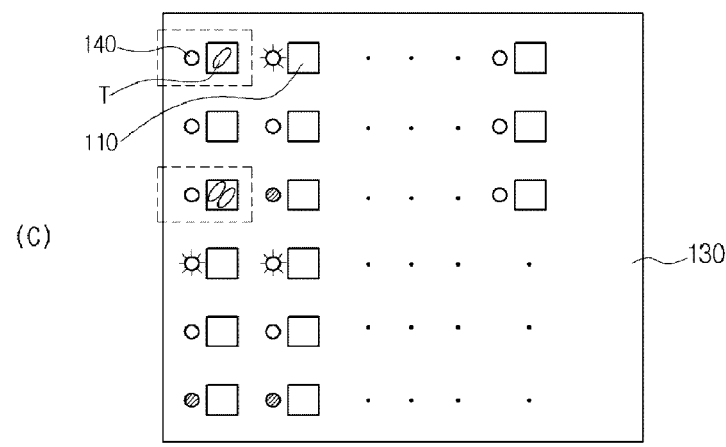
(C)

APPARATUS FOR DISPENSING TABLETS AND METHOD FOR CONTROLLING THE SAME

TECHNICAL FIELD

The present invention relates to an apparatus for dispensing tablets and a method for controlling the same, and more particularly, to an apparatus for dispensing tablets, which is improved in accuracy and simplicity when tablets are dispensed into a tray according to patient's prescription and a method for controlling the same.

BACKGROUND ART

In general, tablet auto-packaging apparatuses may be apparatuses for simultaneously or independently auto-packaging tablets accommodated in a tablet cassette and tables that are not capable of being accommodated in the tablet cassette for single dosage.

Here, a large amount of tablets accommodated in the tablet cassette may be stored at a predetermined position within a tablet auto-packing apparatus and then automatically dispensed as necessary. However, tablets, that are not capable of being accommodated in the tablet cassette, may be automatically dispensed into a separate tray by mounting the separate tray into the tablet auto-packing apparatus after the tray used for dispensing tablets is separately prepared whenever the tablets are needed.

Thus, it may be necessary to manually pre-dispense the tablets, which are not capable of being accommodated in the tablet cassette, into a tray by a user such as pharmacists. That is to say, a process for manually dispensing tablets, which are not capable of being accommodated in the tablet cassette, among tablets written on a prescription into the tray is necessarily required.

When the manual dispensing process as described above is completed, the user such as pharmacists has to check the tablets dispensed into the tray one by one. Then, if it is determined that the dispensing is normal after the checking, the tray may be inserted into the tablet auto-packaging apparatus to operate the tablet auto-packaging, thereby supplying and packing the tablets within the tablet cassette and the tablets dispensed into the tray for single dosage.

Here, the dispensing of the tablets into the tray may be manually realized by the user such as the pharmacists as described above. However, the accuracy in dispensing may be essentially reduced on characteristics of the manual action.

Thus, even though the dispensing of the tablets into the tray is completed, an additional checking process may be necessarily required to reduce work efficiency.

Also, even though the user such as the pharmacists checks whether the tablets are accurately dispensed, it may be difficult to accurately obverse the dispensing of the tablets through a naked eye of the user. Thus, the smallest mistake in dispensing could lead to a serious problem, resulting in damaging patient healthy due to tablet dosing errors.

Also, when the tablets that are not capable of being accommodated in the tablet cassette are manually dispensed into the tray, dusts generated by the tablets due to the repeated usage of the apparatus may remain in the apparatus.

When other tablets are dispensed, the dusts have to be frequently removed to prevent the dusts from being mixed with other tablets. Thus, a separate cleaning process may be required. However, this cleaning process may be more trouble to deteriorate efficiency in work.

Thus, when the tablets are manually dispensed into the tray, studies for improving accuracy in dispensing to realize packing of the tablets that coincide with patient's prescription and for effectively removing the dusts to maximize work efficiency are urgently necessary.

DISCLOSURE OF THE INVENTION

Technical Problem

The objective of the present invention is to provide an apparatus for dispensing tablets, which is capable of maximizing accuracy in dispensing according to the prescription and minimizing a time taken for dispensing to improve efficiency in dispensing when tablets, which are not previously accommodated in a tablet cassette, are manually dispensed into a tray.

Technical Solution

An apparatus for dispensing tablets according to an embodiment of the present invention includes a main body including a plurality of tablet input parts to collect the inputted tablets in a tray disposed therein; and at least one input sensor disposed in the main body to sense whether the tablets are inputted.

The input sensor of the apparatus for dispensing the tablets according to an embodiment of the present invention may include a light emitting device and light receiving device which are disposed on one surface defining each of the tablet input parts and the other surface facing the one surface.

A light irradiation area defined by the light emitting device of the apparatus for dispensing the tablets according to an embodiment of the present invention may have a cross-sectional area in a transverse direction of the tablet input part.

The apparatus for dispensing the tablets according to an embodiment of the present invention may further include the tray collecting the tablets inputted through the tablet input part, wherein the main body may include a cover part in which the tablet input parts are defined and a support part supporting the cover part so that the cover is rotatable and on which the tray is disposed.

The apparatus for dispensing the tablets according to an embodiment of the present invention may further include at least one dust adsorption part detachably disposed on the tablet input parts to remove dusts generated by the input of the tablets.

At least a portion of the dust adsorption part of the apparatus for dispensing the tablets according to an embodiment of the present invention may be formed so that light is transmitted therethrough or is formed transparently.

The main body of the apparatus for dispensing the tablets according to an embodiment of the present invention may include at least one light emitting unit for distinguishing whether the tablets are inputted.

The apparatus for dispensing the tablets according to an embodiment of the present invention may further include at least one dust adsorption part detachably disposed on the tablet input parts to remove dusts generated by the input of the tablets, wherein light emitted from the light emitting unit may be transmitted through the dust adsorption part so as to be distinguished.

The main body of the apparatus for dispensing the tablets according to an embodiment of the present invention may include a plurality of light emitting units for distinguishing whether the tablets are inputted, and the apparatus for dispensing the tablets according to an embodiment of the present invention may further include: the tray collecting the tablets inputted through the tablet input parts; and a control unit acquiring information with respect to the tablets to be inputted into at least a portion of the plurality of tablet input parts to control the plurality of light emitting units on the basis of the acquired information and change a light emitting state of each of the plurality of light emitting units on the basis of the result obtained by sensing of the input sensor.

The information with respect to the tablets to be inputted in the apparatus for dispensing the tablets according to an embodiment of the present invention may include at least one of kinds of tablets, an amount of tablets to be inputted, and an inputting position of tablets.

The control unit of the apparatus for dispensing the tablets according to an embodiment of the present invention may select one of the plurality of kinds of tablets when the kinds of tablets to be inputted are provided in plurality, confirm at least one tablet input part through which the selected kind of tablets are inputted, and control the light emitting state of the light emitting unit corresponding to the confirmed at least one tablet input part.

The control unit of the apparatus for dispensing the tablets according to an embodiment of the present invention may acquire an amount of tablets to be inputted into a first tablet input part of the plurality of tablet input parts from the information with respect to the tablets to be inputted and control the light emitting state of the light emitting unit corresponding to the first tablet input part according to the amount of tablets to be inputted.

The control unit of the apparatus for dispensing the tablets according to an embodiment of the present invention may count an input number of tablets to be inputted into a second tablet input part of the plurality of tablet input parts to change the light emitting state of the light emitting unit corresponding to the second tablet input part.

The control unit of the apparatus for dispensing the tablets according to an embodiment of the present invention may acquire the kind of tablets on the basis of the information with respect to the tablets to be inputted and control the light emitting unit so that the light emitting unit emits light in the light emitting state corresponding to the acquired kind of tablets.

The control unit of the apparatus for dispensing the tablets according to an embodiment of the present invention may control the light emitting unit so that a first light emitting state corresponding to a first kind of tablets is different from a second light emitting state corresponding to a second kind of tablets.

A method for controlling an apparatus for dispensing tablets according to another embodiment of the present invention includes: acquiring information with respect to the tablets to be inputted into at least a portion of the plurality of tablet input parts provided in a tray; controlling a plurality of light emitting units corresponding to the plurality of tablet input parts on the basis of the acquired information; and changing light emitting states of the plurality of light emitting units on the basis of the result obtained by sensing of an input sensor for sensing whether the tablets are inputted into the plurality of tablet input parts.

The method for controlling the apparatus for dispensing the tablets according to another embodiment of the present invention may further include selecting one of a plurality of kinds of tables when the kinds of tablets to be inputted are provided in plurality; and confirming at least one tablet input part, into which the selected kind of tablets has to be inputted, of the plurality of tablet input parts.

The controlling of the light emitting units in the method for controlling the apparatus for dispensing the tablets according to another embodiment of the present invention may include controlling a light emitting state of the light emitting unit corresponding to the confirmed at least one tablet input part.

The controlling of the light emitting units in the method for controlling the apparatus for dispensing the tablets according to another embodiment of the present invention may include controlling the plurality of light emitting units so that the light emitting state of the light emitting unit corresponding to the confirmed at least one tablet input part is different from those of the remaining light emitting units except for the confirmed at least one tablet input part of the plurality of tablet input parts.

The controlling of the light emitting units in the method for controlling the apparatus for dispensing the tablets according to another embodiment of the present invention may include acquiring an input amount of tablets to be inputted into a first tablet input part from the information with respect to the tablets to be inputted; and controlling a light emitting state of the light emitting unit corresponding to the first tablet input part according to the input amount of tablets.

The method for controlling the apparatus for dispensing the tablets according to another embodiment of the present invention may further include counting an input number of tablets to be inputted into a second tablet input part of the plurality of tablet input parts; and changing a light emitting state of the light emitting unit corresponding to the second tablet input part according to the input number of tablets.

Advantageous Effects

According to the apparatus for dispensing the tablets of the present invention, the tablets that are not previously accommodated in the tablet cassette may be accurately and efficiently manually dispensed into the tray that is inserted into the apparatus for automatically dispensing packing the tablets.

Also, the dusts generated while the tablets are manually dispensed may be efficiently removed to minimize the mixing with other tablets.

Also, the manual dispensing may be accurately performed, and the time taken for manually dispensing the tablets may be reduced to maximize the work efficiency.

Also, the tray that is used for manually dispensing the tablets may be easily accurately mounted so that non-skilled persons have an excellent use of the apparatus.

Also, the user such as pharmacists may induce the dispensing of the tablets into the tray in the intuitive method.

BRIEF DESCRIPTION OF THE DRAWINGS

FIG. 14 is a schematic bottom perspective view of the apparatus for dispensing the tablets according to the present invention, FIG. 15 is a schematic exploded perspective view of the apparatus for dispensing the tablets according to the present invention, and FIG. 16 is a schematic view of a state before the tray provided in the apparatus for dispensing the tablets is seated on the main body according to the present invention.

FIGS. 17 and 18 are a schematic view and schematic plan view illustrating a process of seating the tray onto the main body, and FIGS. 19 and 20 are a schematic view and schematic plan view illustrating a process in which the tray is seated on the main body and then fixed to the main body by using a pressing part.

FIG. 24 is a view illustrating one example of prescription information obtained from the apparatus for dispensing the tablets according to the present invention.

FIG. 28 is a view for explaining an example of changing a light emitting state of the light emitting unit of the apparatus for dispensing the tablets according to the present invention.

FIG. 29 is a view for explaining another example of changing the light emitting state of the light emitting unit of the apparatus for dispensing the tablets according to the present invention.

BEST MODE FOR CARRYING OUT THE INVENTION

Figure 1:
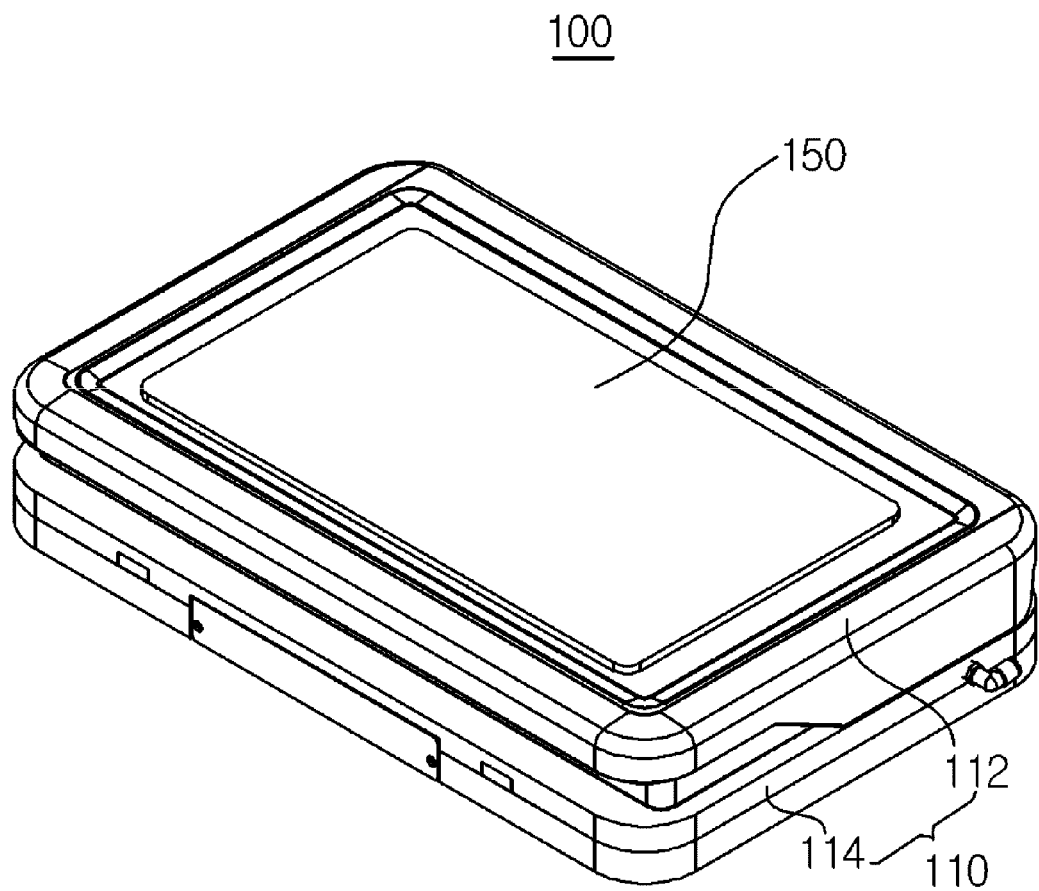
FIG. 1 is a schematic perspective view illustrating a state in which an apparatus for dispensing tablets is folded according to an embodiment of the present invention.

An apparatus for dispensing tablets according to an embodiment of the present invention includes a main body including a plurality of tablet input parts to collect the inputted tablets in a tray disposed therein; and at least one input sensor disposed in the main body to sense whether the tablets are inputted.

MODE FOR CARRYING OUT THE INVENTION

Hereinafter, exemplary embodiments will be described in detail with reference to the accompanying drawings. The invention may, however, be embodied in many different forms and should not be construed as being limited to the embodiments set forth herein; rather, that alternate embodiments included in other retrogressive inventions or falling within the spirit and scope of the present disclosure will fully convey the concept of the invention to those skilled in the art.

Also, the components having the same function are quoted by the same reference numeral throughout the drawings for explaining the embodiments.

Figure 2:
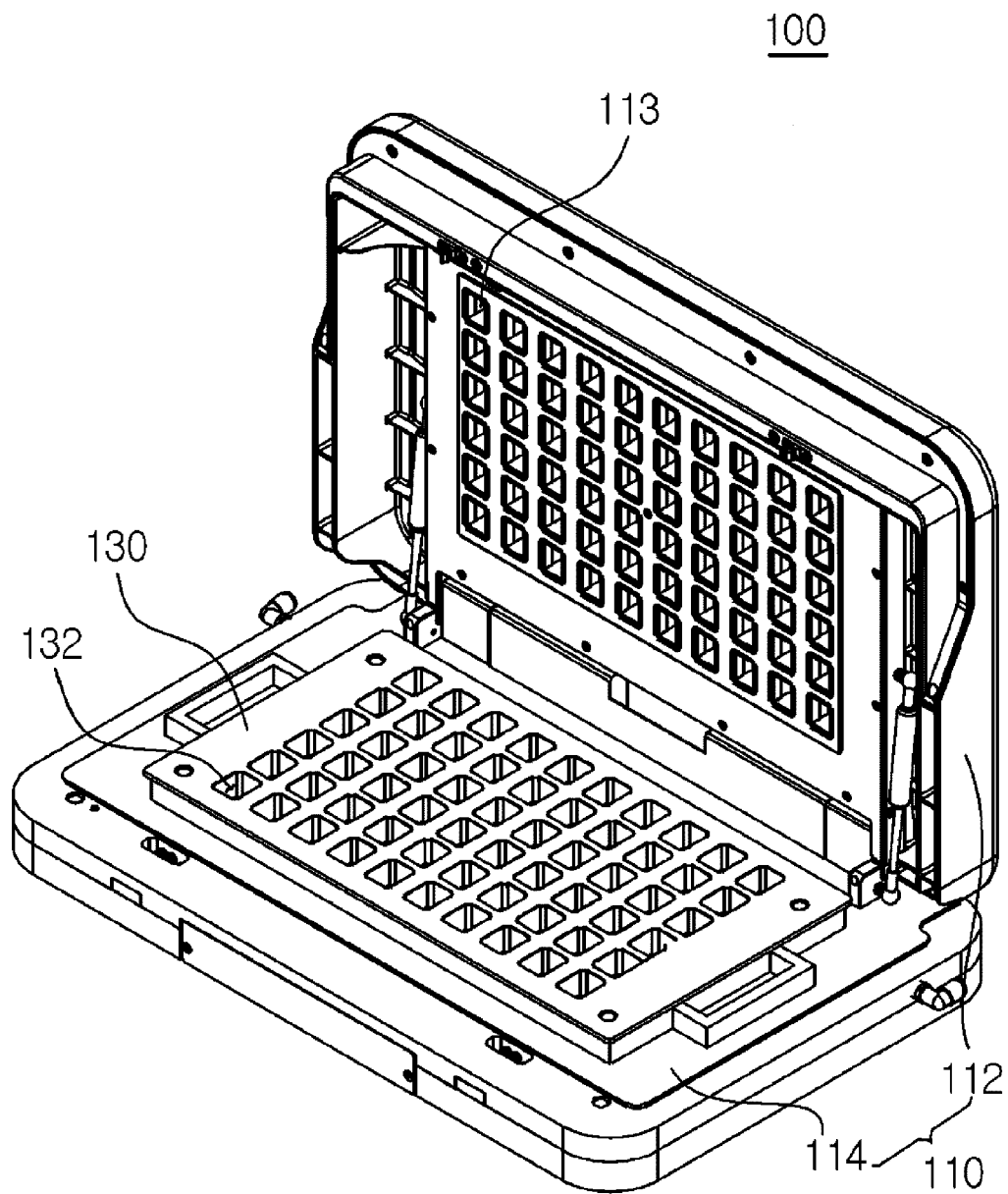
FIG. 2 is a schematic perspective view illustrating a state in which the apparatus for dispensing the tablets is unfolded according to an embodiment of the present invention.
Figure 3:
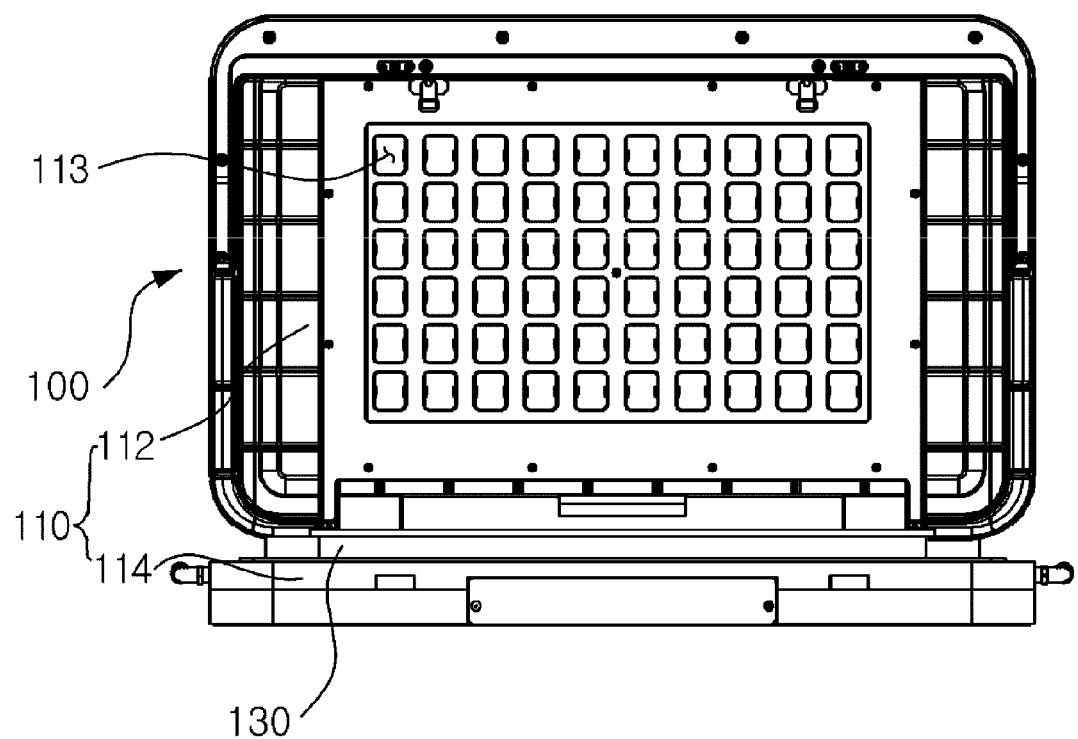
FIG. 3 is a schematic front view illustrating the state in which the apparatus for dispensing the tablets is unfolded according to an embodiment of the present invention.

FIG. 1 is a schematic perspective view illustrating a state in which an apparatus for dispensing tablets is folded according to an embodiment of the present invention, FIG. 2 is a schematic perspective view illustrating a state in which the apparatus for dispensing the tablets is unfolded according to an embodiment of the present invention, and FIG. 3 is a schematic front view illustrating the state in which the apparatus for dispensing the tablets is unfolded according to an embodiment of the present invention.

Figure 4:
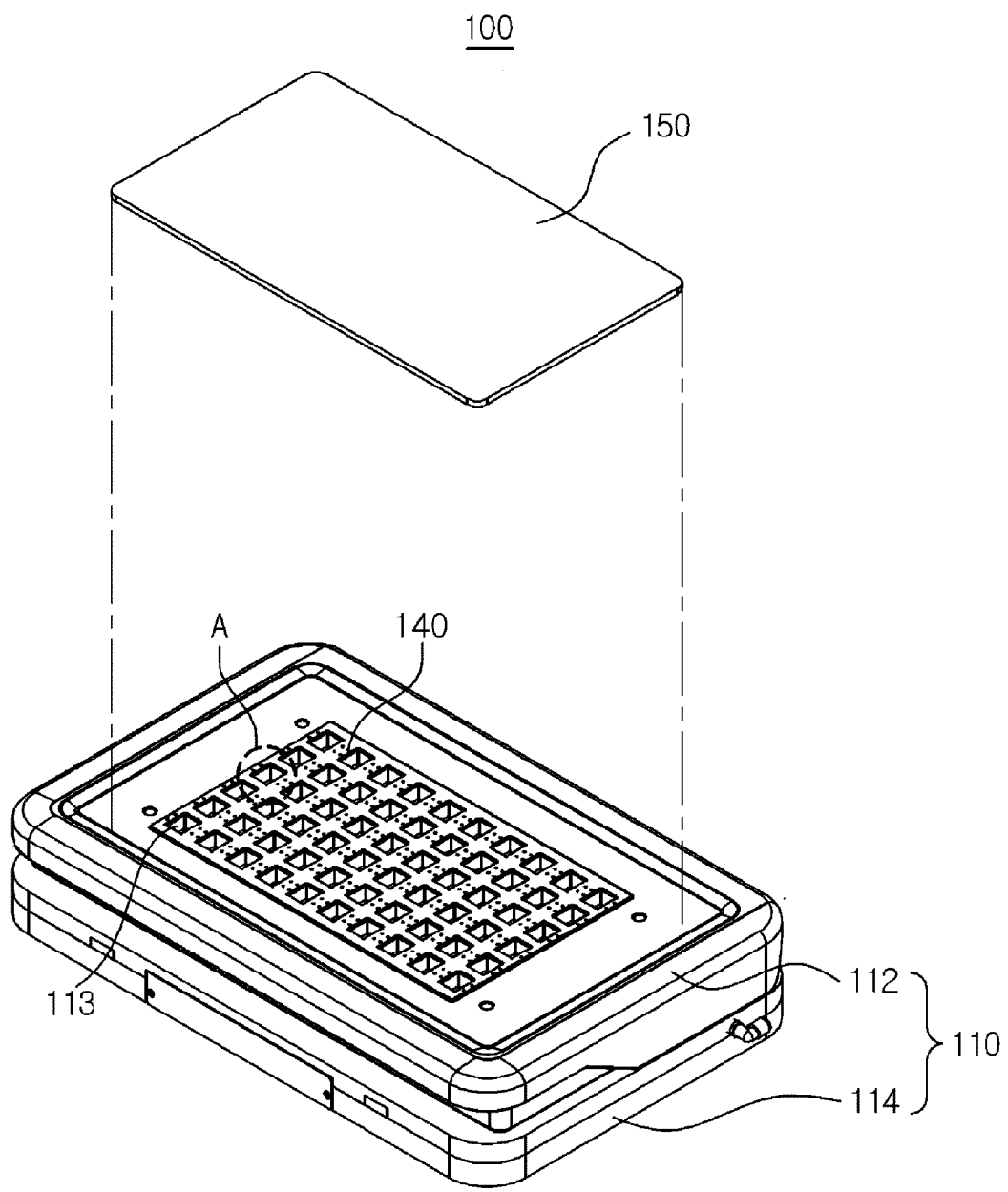
FIG. 4 is a schematic perspective view illustrating a state in which a protection cover is separated from the apparatus for dispensing the tablets according to an embodiment of the present invention.
Figure 5:
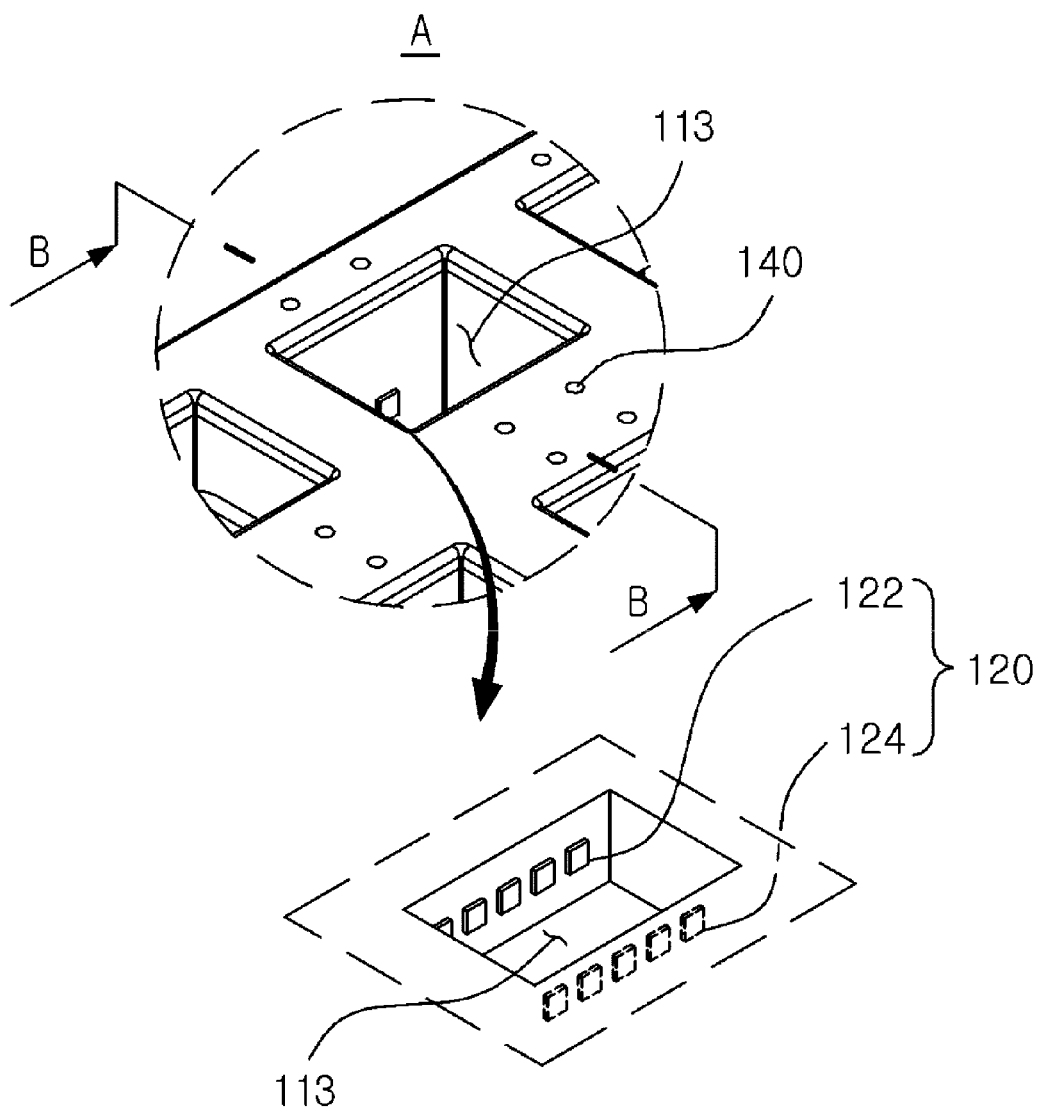
FIG. 5 is a schematic enlarged view of a portion A of FIG. 4.
Figure 6:
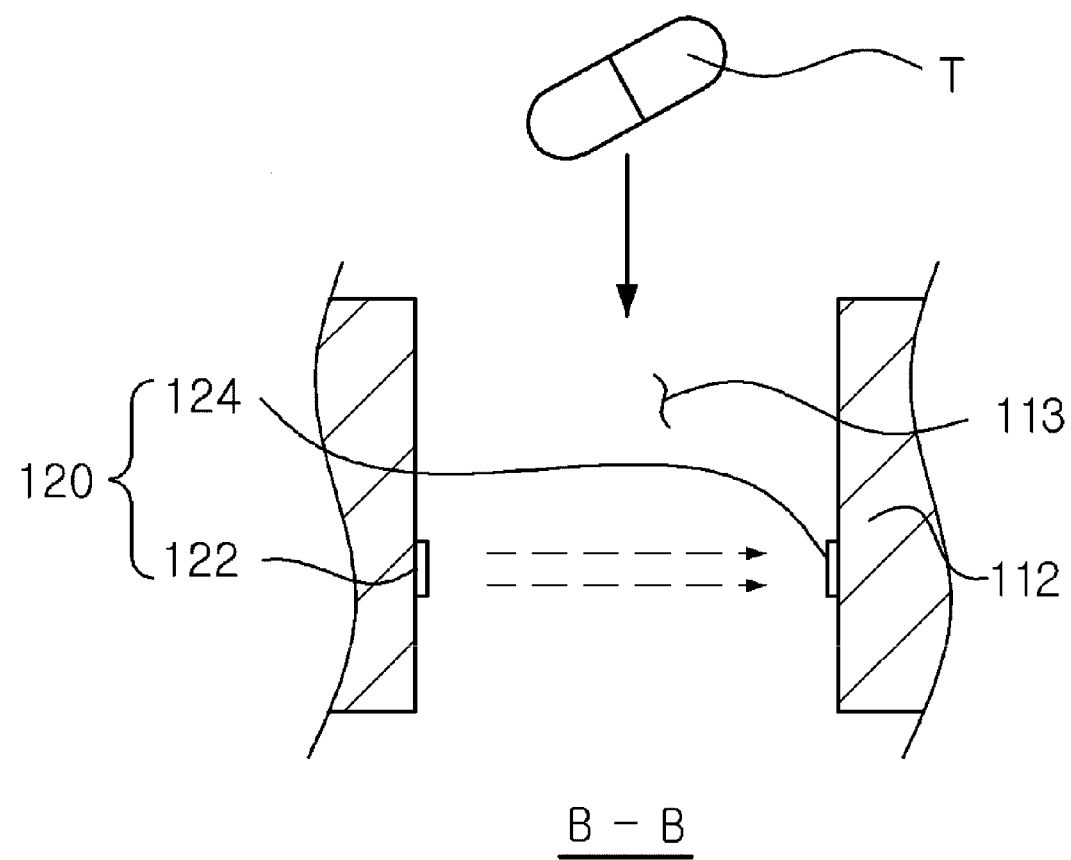
FIG. 6 is a schematic cross-sectional view taken along line B-B of FIG. 5, i.e., a schematic view for explaining an operation principle of an input sensor disposed in the apparatus for dispensing the tablets according to an embodiment of the present invention.

Also, FIG. 4 is a schematic perspective view illustrating a state in which a protection cover is separated from the apparatus for dispensing the tablets according to an embodiment of the present invention, FIG. 5 is a schematic enlarged view of a portion A of FIG. 4, and FIG. 6 is a schematic cross-sectional view taken along line B-B of FIG. 5, i.e., a schematic view for explaining an operation principle of an input sensor disposed in the apparatus for dispensing the tablets according to an embodiment of the present invention.

Figure 7:
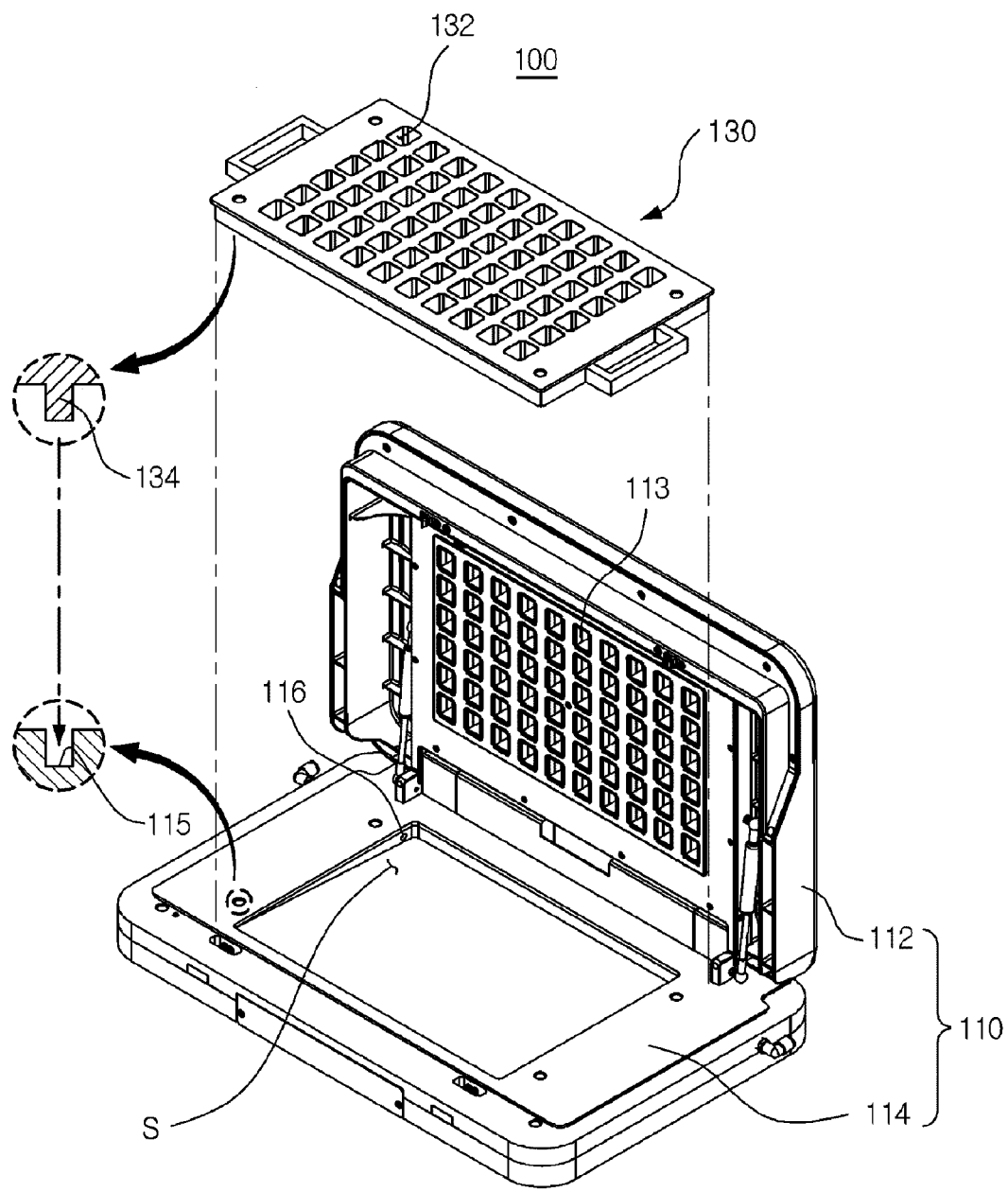
FIG. 7 is a schematic perspective view illustrating a state in which the apparatus for dispensing the tablets is unfolded, and the tray is disassembled according to an embodiment of the present invention.

FIG. 7 is a schematic perspective view illustrating a state in which the apparatus for dispensing the tablets is unfolded, and the tray is disassembled according to an embodiment of the present invention.

Referring to FIGS. 1 to 7, an apparatus 100 for dispensing tablets (hereinafter, referred to as a tablet dispensing apparatus) according to an embodiment of the present invention may be an apparatus for dispensing tablets into a tray 130. For example, the tablet dispensing apparatus 100 may be an apparatus for separating the tray in which the dispensing of the tablets is completely performed and then inserting a new tray to repeatedly perform the manual dispensing of the tablets into the tray 130.

That is, when the dispensing of the tablets into the tray 130 is completely performed by using the tablet dispensing apparatus 100 according to an embodiment of the present invention, the tray 130 may be inserted into a tablet auto-packing apparatus (not shown). The tablet auto-packing apparatus may pack the tablets within a tablet cassette and the tablets dispensed into the tray 130 for single dosage according to the patient's prescription.

That is, while the tray 130 into the tablets are completely dispensed is inserted to operate the tablet auto-packing apparatus, the tablet dispensing apparatus 100 may be repeatedly operated to prepare a plurality of trays into which the tablets are completely dispensed. Thus, a stopping time of the tablet auto-packing apparatus, which is taken for inserting the tray 130 into the tablet auto-packing apparatus may be minimized.

Particularly, the tablet dispensing apparatus 100 according to an embodiment of the present invention may include a main body 110 including a plurality of tablet input parts 113 and an input sensor 120 disposed in the main body 110 to sense whether the tablets are dispensed.

The main body 110 may define an outer appearance of the tablet dispensing apparatus 100 and may include a support part 114 for supporting a bottom surface on which the tablet dispensing apparatus 100 is placed and a cover part 112 that is coupled to be rotatable at a predetermined angle from one side of the support part 114.

That is, the main body 110 may have a predetermined space in which the tray 130 for collecting the tablets inputted through the tablet input part 113 is disposed when the cover part 112 and the support part 114 are folded.

Here, the cover part 112 of the main body 110 may include the plurality of tablet input parts 113 that communicate with the space to collect the tablets into the tray 130. Thus, a user such as a pharmacist may input the tablets into the tray 130 through the tablet input parts 113.

That is, each of the tablet input parts 113 may be a kind of hole through which the tablets pass. When the tray 130 is disposed on the main body 110, and the tablet dispensing apparatus 100 is folded, the tablet input parts may be disposed to correspond to tablet collection parts 132 disposed in the tray 130, respectively.

The plurality of tablet input parts 113 may be longitudinally and transversely disposed to pass through the cover part 112. When the cover part 112 is folded with respect to the support part 114, the tablet input parts 113 may be disposed to correspond to the tablet collection parts 132 of the tray 130 disposed on the support part 114, respectively.

Whether the tablets are inputted through the tablet input parts 113 may be sensed by the input sensor 120.

The input sensor 120 may be realized in various manners.

First, the input sensor 120 may sense whether the tablet T passes through the tablet input part 113.

For example, the input sensor 120 may be mounted on at least one surface defining the tablet input part 113. The input sensor 120 may include a light emitting device 122 and a light receiving device 124, which are respectively disposed on the one surface defining the tablet input part 113 and the other surface facing the one surface. Thus, the light emitting device 122 of the input sensor 120 may continuously emit light onto the light receiving device 124. Thus, whether the tablet T is inputted may be sensed through momentary interruption of the light emitted onto the light receiving device 124 due to the input of the tablet T. Here, at least two of each of the light emitting device 122 and the light receiving device 124 may be disposed along the one surface defining the tablet input part 113 and the other surface facing the one surface. When each of the light emitting devices 122 and the light receiving devices 124 is provided in plurality, whether the tablet T that is inputted into the tray 130 by passing through the tablet input part 113 may be accurately sensed.

Second, the input sensor 120, although not shown in the drawings, may be disposed in the vicinity of the bottom surface of the tablet input part 113 to sense a pressure applied to the bottom surface of the tablet input part 113.

For example, when the tablets are inputted into the tablet input part 113 by the tablet dispensing operation of the pharmacist, a pressure may be applied to the bottom surface of the tablet input part 113 by weights of the inputted tablets. Thus, whether the tablets are inputted into the tablet input part 113 may be confirmed by the sensed pressure.

Third, although not shown in the drawings, the input sensor 120 may be disposed on one side of the tablet input part 100 to sense vibration of the tablet input part 113.

For example, when the tablets are inputted into the tablet input part 113 by the tablet dispensing operation of the pharmacist, vibration may occur by impacts of the inputted tablets against a side surface and/or bottom surface of the tablet input part 113. Thus, whether the tablets are inputted into the tablet input part 113 may be confirmed by the sensed vibration.

Hereinafter, for convenience of description, the input sensor 120 including a pair of light emitting device 122 and light receiving device 124 will be exemplified.

The input sensor 120 may sense the preset inputted number of tablet T and thus sense whether the incorrect number of tablet T is inputted.

Particularly, the input sensor 120 may be mounted on at least one surface defining the tablet input part 113. The input sensor 120 may include the light emitting device 122 and the light receiving device 124, which are respectively disposed on the one surface defining the tablet input part 113 and the other surface facing the one surface.

Here, at least one of each of the light emitting device 122 and the light receiving device 124 may be disposed along the one surface defining the tablet input part 113 and the other surface facing the one surface.

That is, a light irradiation area due to the light emitting device 122 may include a cross-section in a transverse direction of the tablet input part 113.

This is done for improving the accuracy in sensing with respect to whether the tablet inputted into the tray 130 by passing through the tablet input part 113 and also for preventing a dead zone from occurring in the tablet input part 113.

Particularly, the light emitting device 122 of the input sensor 120 may continuously emit light onto the light receiving device 124. Thus, whether the tablet is inputted may be sensed through momentary interruption of the light emitted onto the light receiving device 124 due to the input of the tablet.

The result sensed by the input sensor 120 with respect to whether the tablet is inputted may be distinguished at the outside by at least one light emitting unit 140 disposed in the main body 110. The light emitting unit 140 may be a light emitting diode (LED).

The light emitting unit 140 may be disposed in the main body 110 that corresponds to at least one side of the tablet input part 113. Also, a light emitting state may be different according to whether the tablet is inputted, i.e., the result obtained by the sensing of the input sensor 120.

That is, if the preset number of tablets is inputted and otherwise, whether the tablet is accurately inputted may be distinguished by using a change in color of the light, flickering light, or a difference in degree of the flickering light.

The light emitted from the light emitting unit 140 may be emitted toward the outside of a top surface of the main body 110 corresponding to at least one side of the tablet input part 113.

That is, since the light emitted from the light emitting unit 140 is emitted toward the outside of the top surface of the cover part 112, the user such as the pharmacist may confirm whether the tablet is accurately inputted by only observing the cover part 112 through a naked eye thereof.

The inside of the tablet dispensing apparatus 100 according to an embodiment of the present invention may be protected against the outside by a protection cover 150. Particularly, the protection cover 150 may cover the tablet input part 113 while the tablet dispensing apparatus 100 is not used to previously prevent foreign substances from being introduced from the outside.

The tray 130 disposed on the support part 114 of the main body 110 may be stably fixed by at least one insertion protrusion 134 and at least one insertion groove 115. Here, the insertion protrusion 134 and the insertion groove 115 may be disposed to correspond to each other.

That is, one of facing surfaces of the tray 130 and the support part 114 may protrude to form the at least one insertion protrusion 134, and the other one of the facing surfaces may be recessed to form the at least one insertion groove 115 so that the insertion protrusion 134 is inserted to guide a position of the tray 130.

Particularly, the insertion protrusion 134 may be provided in plurality to protrude from a bottom surface of the tray 130. The insertion groove 115 may be recessed from the top surface of the support part 114 to correspond to the insertion protrusion 134.

Thus, in a case where the tray 130 is disposed on the support part 114, when the insertion protrusion 134 is inserted into the insertion groove 115, the tray 130 may be guided in position to stably fix the tray 130 to the support part 114.

Here, a collection space S into which dusts of the tablets dispensed into the tray 130 are collected may be defined in the top surface of the support part 114 facing the bottom surface of the tray 130. The collection space S may have a depth that gradually increases toward one side of the support part 114.

That is, the collection space S may provide a space into which the dusts of the tablets, which the tablets are inputted into the tray 130 through the tablet input part 113 and while are generated while the tray 130 is separated from the main body 110 after the cover 112 rotates from the support part 114 to minimize an effect due to the dusts.

Here, the collection space S may communicate with the outside by a communication part 116. The dusts collected into the collection space S may be discharged to the outside through the communication part 116.

That is, the communication part 116 may be defined in one side of the collection space S, i.e., a portion having the deepest depth. The communication part 116 may be connected to an external suction device (not shown) to discharge the dusts collected into the collection space S to the outside by using a suction force of the suction device.

However, the formation position of the communication part 116 is not limited to the one side of the collection space S. As long as the dusts collected into the collection space S are discharged through the communication part 116, the communication part 116 is not limited to its formation position.

Hereinafter, the overall operation order of the tablet dispensing apparatus 100 according to an embodiment of the present invention will be described.

First, the tray 130 is disposed in an inner space of the main body 110, i.e., an upper side of the collection space S of the support part 114.

Here, the insertion protrusion 134 disposed on the tray 130 may be inserted into the insertion groove 115 defined in the support part 114 to stably fix the tray 130 to the support part 114.

When the tray 130 is fixed to the support part 114, and the cover part 112 is closed, a position of the tablet input part 113, which corresponds to a portion into which the tablet T is inputted according to the patient's prescription may be displayed on a display (not shown).

Simultaneously, the light emitting unit 140 disposed in the main body 110 may emit light having a predetermined color, like the display. Here, since the light having the predetermined color is emitted toward the outside of the top surface of the cover part 112, the user may distinguish the input of the tablet T from the outside.

Then, the user such as the pharmacist may input the tablet T into the tablet input part 113 according to whether light is emitted from the light emitting unit 140, and the input sensor 120 may accurately sense the input of the tablet T while the tablet T is inputted.

That is, the input sensor 120 may sense the input of the tablet according to whether the light emitted from the light emitting device 122 toward the light emitting device 124 is interrupted. Here, when the accurate input of the tablet is performed, the light emitting unit 140 may change in light emitting state by an electrical signal of a control unit (not shown).

If the accurate input of the tablet is not performed, i.e., when at least two grains of tablets T are inputted into the tablet input part 113 into which one grain of tablet T has to be inputted, the light emitted from the light emitting unit 140 may change in light emitting state, i.e., may be flickered or change in color so that the user is capable of distinguishing the change in light emitting state.

In this case, the user may take the tablet T that is incorrectly inputted into the tablet input part 113 out to correct the incorrect input of the tablet T. When the incorrect input is completely corrected, the light emitting unit 140 may change in light emitting state to allow the user such as the pharmacist to distinguish the corrected input of the tablet T.

When the above-described process is completely performed, the cover part 112 may rotate to separate the tray 130 into the tablet is inputted and then to mount a new tray, thereby repeatedly performing the above-described processes.

The light emitted from the light emitting unit 140 may change in color in the tablet input part 113 into which the tablet has to be inputted. This may be an expression in a case where the number of tablet to be inputted into one tablet input part 113 changes.

This may be automatically controlled according to the prescription contained in the tray 130 and then be displayed on the display. The user such as the pharmacist may easily determine the controlled state with reference to the display.

As described above, the dusts of the tablets, which the tablets are inputted into the tray 130 through the tablet input part 113 and while are generated while the tray 130 is separated from the main body 110 after the cover 112 rotates from the support part 114 may be discharged to the outside through the communication part 116 defined in the collection space S.

Thus, in the tablet dispensing apparatus 100 according to an embodiment of the present invention, the tablets may be accurately manually dispensed into the tray 130 by the input sensor 120 and the light emitting unit 140, and also, the accuracy in the manual dispensing may be realized.

Also, the time taken for manually dispensing the tablets may be reduced to maximize efficiency in work.

Figure 8:
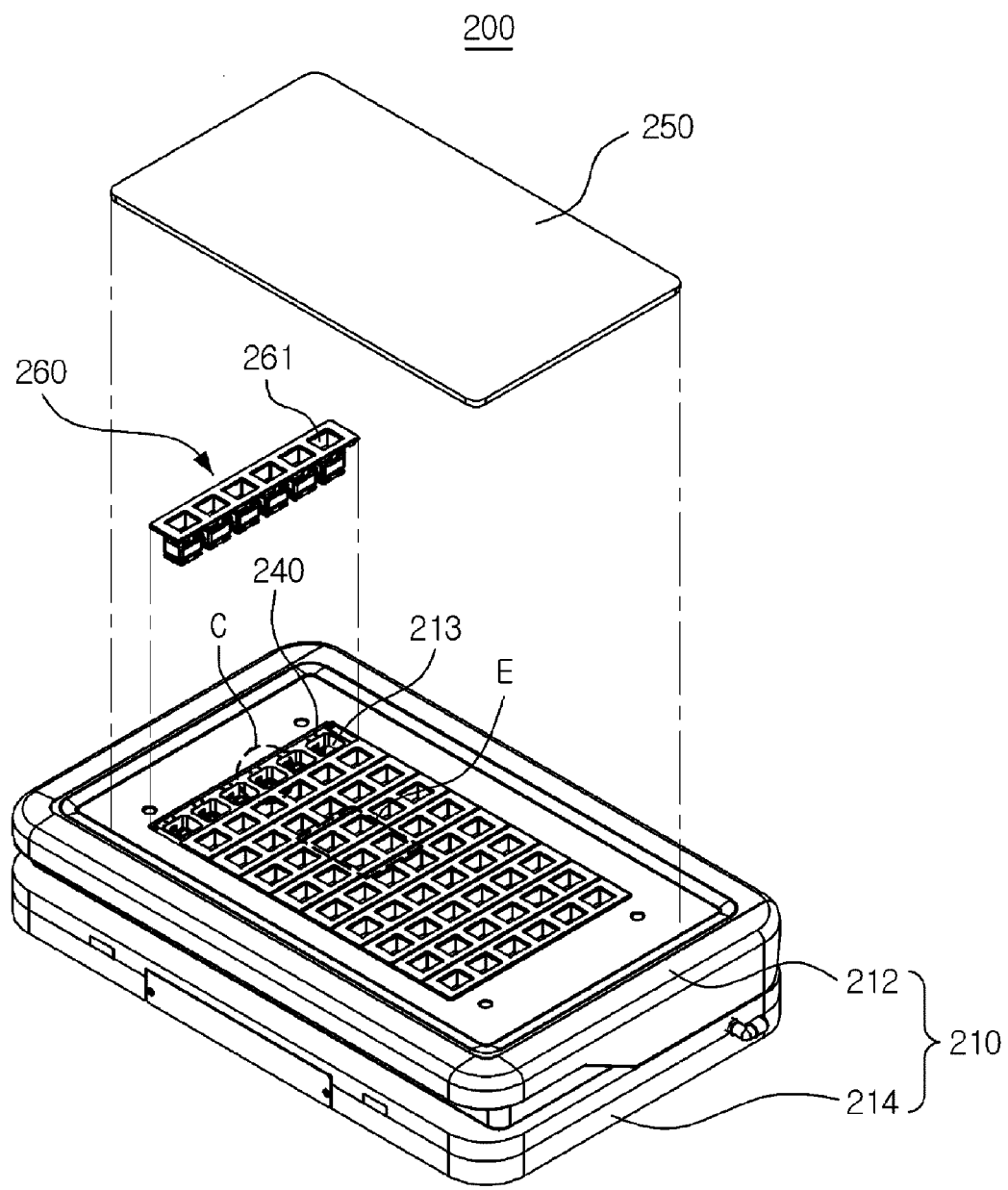
FIG. 8 is a schematic exploded perspective view of an apparatus for dispensing tablets according to another embodiment of the present invention.
Figure 9:
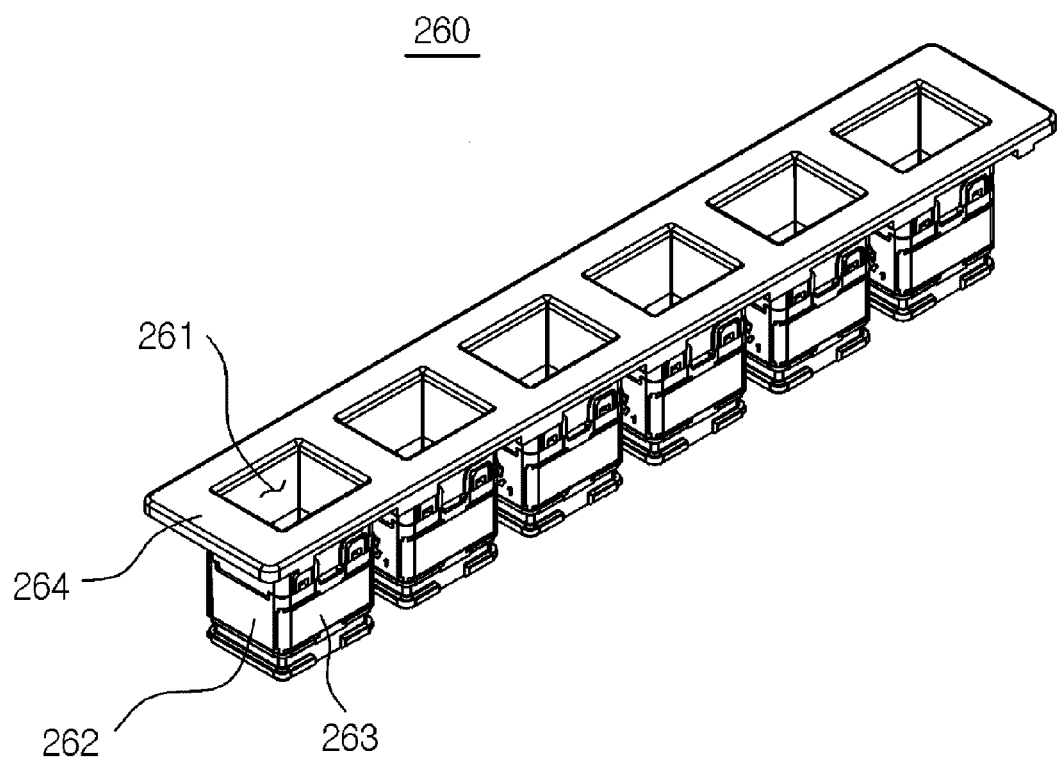
FIG. 9 is a schematic perspective view of a dust adsorption part disposed in the apparatus for dispensing the tablets according to another embodiment of the present invention.

FIG. 8 is a schematic exploded perspective view of an apparatus for dispensing tablets according to another embodiment of the present invention, and FIG. 9 is a schematic perspective view of a dust adsorption part disposed in the apparatus for dispensing the tablets according to another embodiment of the present invention.

Figure 10:
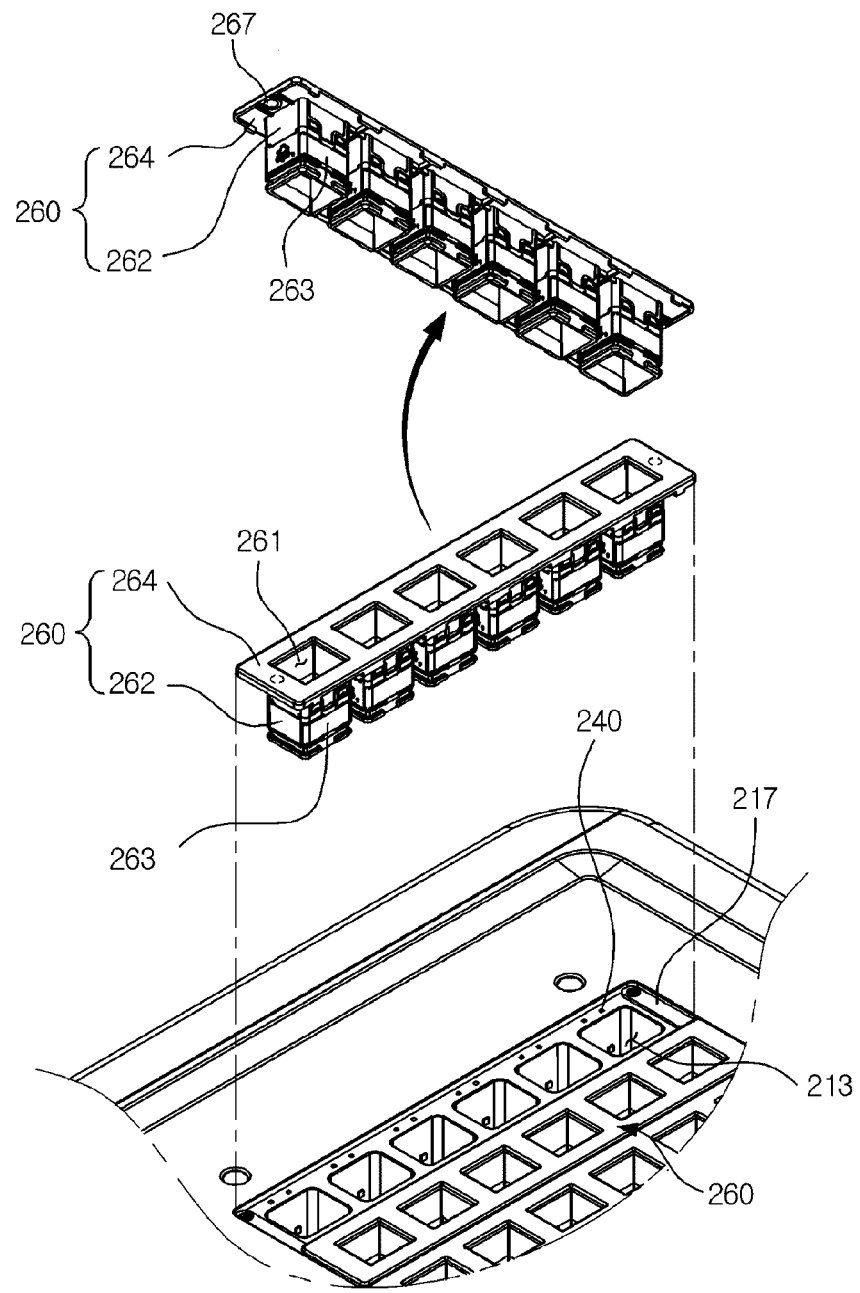
FIG. 10 is a schematic exploded perspective view of a coupling relationship between the dust adsorption part and a main body which are disposed in the apparatus for dispensing the tablets according to another embodiment of the present invention.
Figure 11:
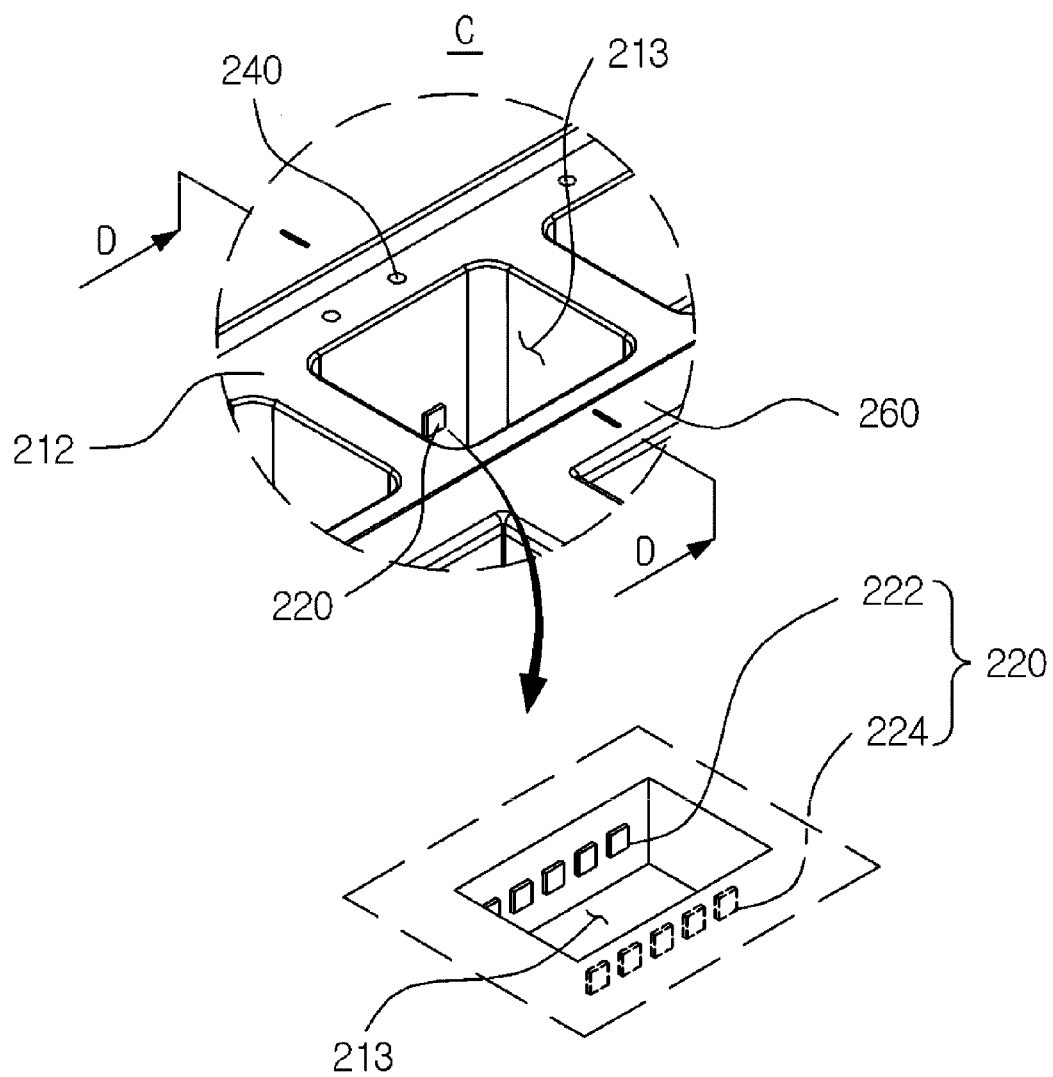
FIG. 11 is a schematic enlarged view of a portion C of FIG. 8.
Figure 12:
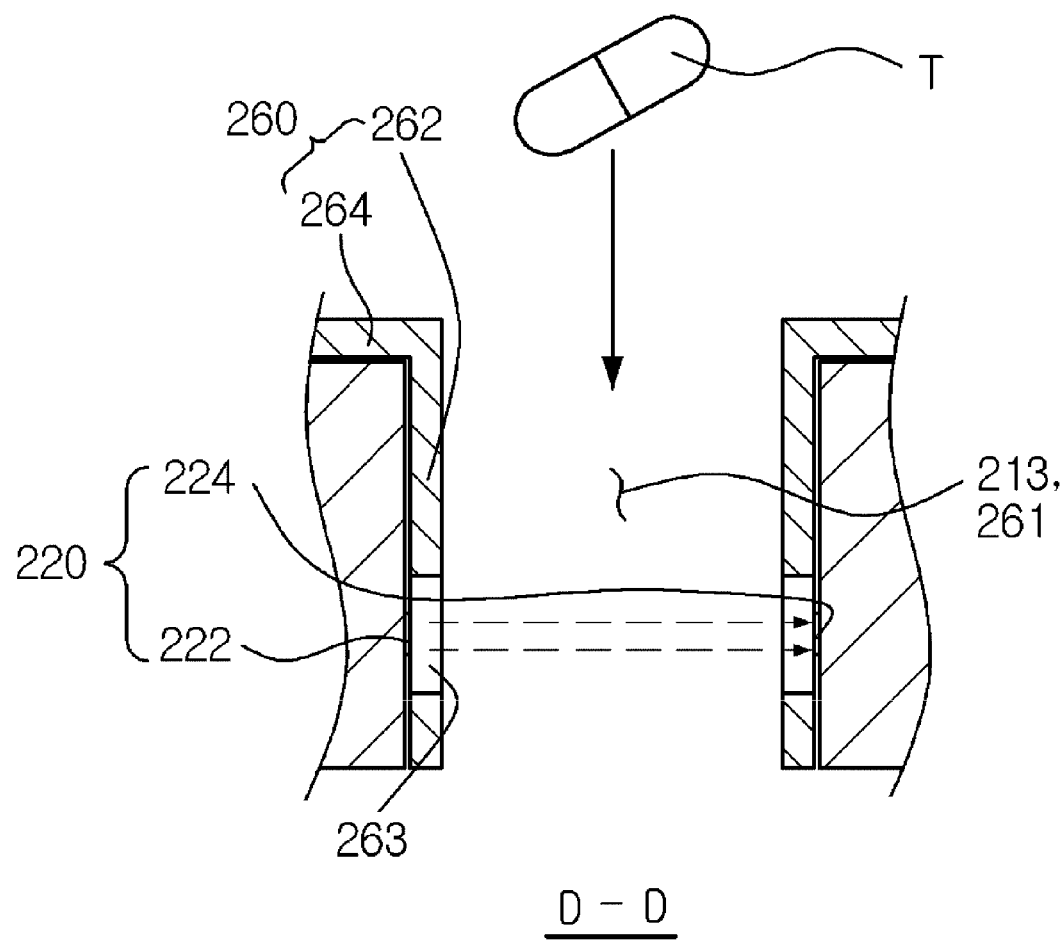
FIG. 12 is a schematic cross-sectional view taken along line D-D of FIG. 11, i.e., a schematic view for explaining an operation principle of an input sensor disposed in the apparatus for dispensing the tablets according to another embodiment of the present invention.

Also, FIG. 10 is a schematic exploded perspective view of a coupling relationship between the dust adsorption part and a main body which are disposed in the apparatus for dispensing the tablets according to another embodiment of the present invention, FIG. 11 is a schematic enlarged view of a portion C of FIG. 8, and FIG. 12 is a schematic cross-sectional view taken along line D-D of FIG. 11, i.e., a schematic view for explaining an operation principle of an input sensor disposed in the apparatus for dispensing the tablets according to another embodiment of the present invention.

Referring to FIGS. 8 to 12, since a tablet dispensing apparatus 200 according to another embodiment of the present invention is the same as that 100 described with reference to FIGS. 1 to 7 according to an embodiment of the present invention except for a dust adsorption part 260, descriptions of other components except for the dust adsorption part 260 will be omitted.

A main body 210 may include a cover part 212 and a support part 214. The dust adsorption part 260 may be detachably inserted into a tablet input part 213 disposed on the cover part 212.

That is, the dust adsorption part 260 may be a kind of structure for removing the dusts generated by the input of the tablets. Thus, the dust adsorption part 260 may be inserted into the tablet input part 213 to previously prevent the dusts generated when the tablets are inputted from contacting all surfaces defining the tablet input part 213, thereby minimizing an amount of dusts remaining in the main body 210.

However, the dusts of the tablets may remain on the dust adsorption part 260. Thus, the dusts remaining on the dust adsorption part 260 may be simply removed by performing a cleaning process after the dust adsorption part 260 is separated from the tablet input part 213.

Particularly, the dust adsorption part 260 may be detachably inserted into the tablet input part 213 and then fixed. Also, the dust adsorption part 260 may include a partition part 262 and a seat part 264.

That is, the dust adsorption part 260 may include the partition part 262 inserted into the tablet input part 213 and the seat part 264 extending from one side of the partition part 262 and seated on a top surface of the cover part 212 that is one component of the main body 210.

The partition part 262 may have an approximately rectangular shape corresponding to that of the tablet input part 213. Also, the partition part 262 may have a through hole 261 through which the tablet pass from the outside.

However, each of the tablet input part 213, the partition part 262, and the through hole 261 is not limited to the approximately rectangular shape. For example, as long as the input of the tablet is performed, each of the tablet input part 213, the partition part 262, and the through hole 261 may have various shapes.

When the partition part 262 is inserted into the tablet input part 213, the contact of the all surfaces defining the tablet input part 213 with the tablet may be prevented by the partition part 262. Thus, an amount of dusts remaining in the main body 210 may be minimized.

Here, the dust adsorption part 260 may be detached on at least portions of the plurality of tablet input parts 213 at the same time. For example, as illustrated in FIGS. 8 to 10, a separate dust adsorption part 260 may be detachably inserted into one row.

That is, the number of dust adsorption part 260 inserted into the tablet input part 213 may variously change. This will be described with reference to FIG. 13. Hereinafter, a case in which a separate dust adsorption part 260 is disposed in one row will be described as an example.

The dust adsorption part 260 may be detachably stably fixed to the main body 210 by a magnetic property thereof. This may be realized by a detachable magnet 267 and a detachment corresponding part 217.

That is, the fixing of the dust adsorption part 260 to the main body 210, i.e., the fixing of the seat part 264 to the cover part 212 may be realized by the detachable magnet 267 disposed on the seat part 264 and the detachment corresponding part 217 disposed on the cover part 212.

That is, the detachable magnet 267 may be a kind of magnet having a magnetic property and be mounted on the seat part 264. The detachment corresponding part 217 reacting with the magnetic property may be disposed on the cover part 212 corresponding to the detachable magnet 267.

Thus, when the dust adsorption part 260 is inserted into the tablet input part 213, the dust adsorption part 260 may be easily and simply detachably fixed to the tablet input part 213 by an attractive force due to the magnetic property.

As described above, the tablet dispensing apparatus 200 according to another embodiment of the present invention may easily remove the dusts generated when the tablet is inputted by using the dust adsorption part 260 that is detachably fixed to the main body 210 to previously prevent the dusts from contacting other tablets to be inputted.

That is, if the tablet input part is directly inputted through the tablet input part without the dust adsorption part, the possibility in attachment of the dusts on one surface defining the tablet input part may be high. In this case, to remove the dusts, the tablet input part has to be cleaned one by one.

On the other hand, since the tablet input part 213 is inserted into the dust adsorption part 260, the dusts of the tablet may be adsorbed onto the dust adsorption part 260. In this case, only the dust adsorption part 260 may be separated from the main body 210 so as to perform a separate cleaning process, thereby easily performing the dust removing process.

Thus, the dusts generated while the tablets are manually dispensed may be efficiently removed to minimize mixing of the dusts with other tablets.

At least a portion 263 of the partition part 262 that is one component of the dust adsorption part 260 may be provided so that light is transmitted therethrough, i.e., may be transparent.

This is done for realizing the accuracy in sensing of the input sensor 220.

That is, the light emitted from the light emitting device 222 of the input sensor 220 may pass through the dust adsorption part 260 to reach the light emitting device 224. For this, at least a portion 263 of the dust adsorption part 260 corresponding to the input sensor 220, i.e., the light emitting device 222 and the light receiving device 224 may be provided so that the light is transmitted therethrough.

Also, at least a portion 263 of the dust adsorption part 260 may be transparent to provide a light transmitting property.

The seat part 264 of the dust adsorption part 260 may be formed of a material that is capable of transmitting the light so that the light emitted from the light emitting unit 240 is distinguished at the outside.

Here, the light emitted from the light emitting unit 240 may be emitted toward the outside of a top surface of the main body 210 corresponding to at least one side of the tablet input part 213. In this case, a path of the light may be covered by the seat part 264 of the dust adsorption part 260.

Thus, the light emitting unit 240 may be distinguished by passing through the seat part 264 of the dust adsorption part 260. For this, the seat part 264 may be formed of a material that is capable of transmitting the light emitted from the light emitting unit 240.

Thus, any obstacles may not be provided so as to distinguish the light emitted from the light emitting unit 140.

The inside of the tablet dispensing apparatus 200 according to another embodiment of the present invention may be protected against the outside by a protection cover 250. Particularly, the protection cover 250 may cover the dust adsorption. part 260 while the tablet dispensing apparatus 200 is not used to previously prevent foreign substances from being introduced from the outside.

Also, the removing of the dusts of the tablets may be simply performed by separating the dust adsorption part 200 from the main body 100 to clean the dust adsorption part 200. Also, as described above, the dusts collected into a collection space S may be discharged to the outside by a suction device mounted on a communication part 108.

In the tablet dispensing apparatus 200, it may be unnecessary to provide the dust adsorption part 200 together with the input sensor 220. That is, the dust adsorption part 200 and the input sensor 220 may be selectively provided.

Figure 13:
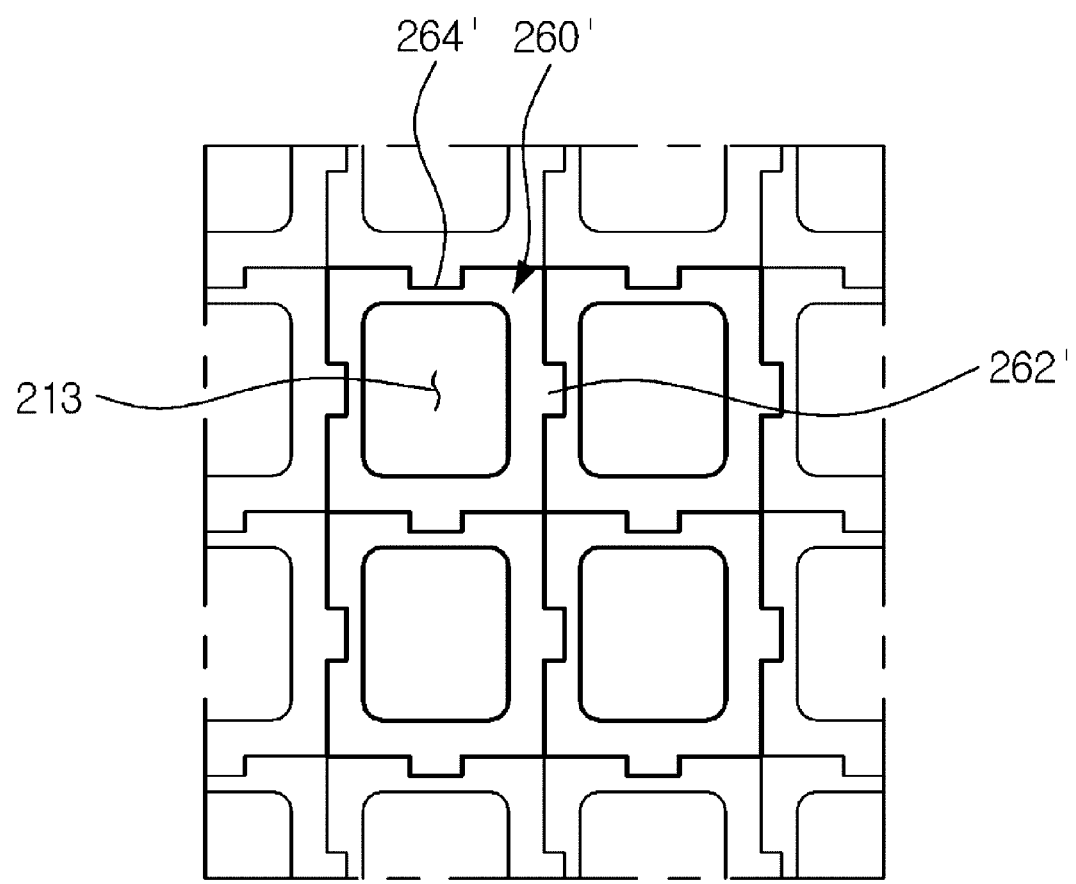
FIG. 13 is a view illustrating a modified example of a portion E of FIG. 8, i.e., a schematic plan view illustrating a modified example of the dust adsorption part disposed in the apparatus for dispensing the tablets according to another embodiment of the present invention.

FIG. 13 is a view illustrating a modified example of a portion E of FIG. 8, i.e., a schematic plan view illustrating a modified example of the dust adsorption part disposed in the apparatus for dispensing the tablets according to another embodiment of the present invention.

Referring to FIG. 13, a dust adsorption part 260' may be detachably coupled to each of the plurality of tablet input parts 213 and also be coupled to an adjacent dost adsorption part 260'.

That is, the dust adsorption part 260' may include a coupling part 262' that protrudes so as to be coupled to the adjacent dust adsorption part 260' and a coupling corresponding part 264' that is recessed. Thus, the components may be coupled to each other to change into various structures.

Thus, the user such as the pharmacist may sort the tablet input part 213 in which a relatively large amount of dusts is generated and couple the dust adsorption parts 260' that are inserted into a corresponding portion of the sorted tablet input part 213 so that the dust adsorption parts 260' are integrated with each other. Thus, efficiency in dust removing may be improved by cleaning only the integrated dust adsorption parts 260' in the dust removing process.

The coupling part 262' and the coupling corresponding part 264' for coupling the dust adsorption parts 260' to each other are not limited to the above-described structures of FIG. 13. For example, each of the coupling part 262' and the coupling corresponding part 264' may have various shapes such as a trapezoid shape or arc shape.

Also, the dust adsorption part 260' inserted into the outermost tablet input part 213 may not include the coupling part 262' and the coupling corresponding part 264' at all of edges thereof.

Figure 14:
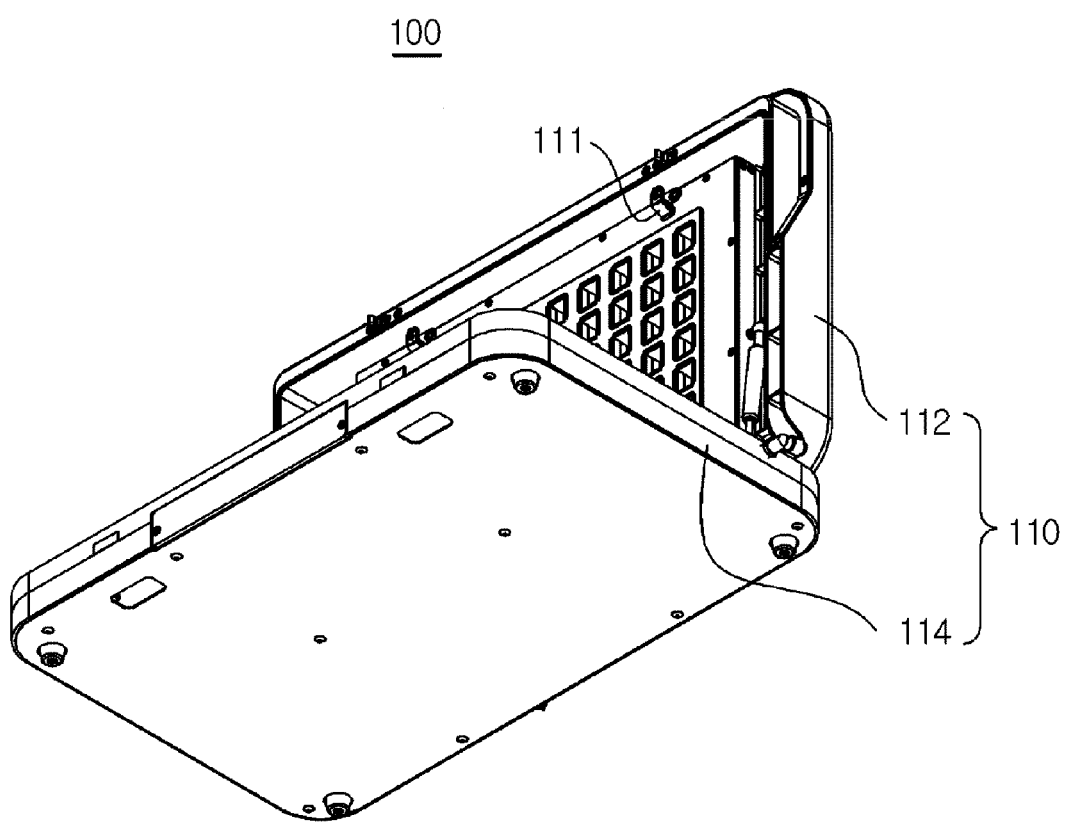
FIGS. 14 to 20 are schematic perspective views illustrating a modified example of a coupling relationship between the main body and the tray which, are disposed in the apparatus for dispensing the tablets according to the present invention, i.e.
Figure 15:
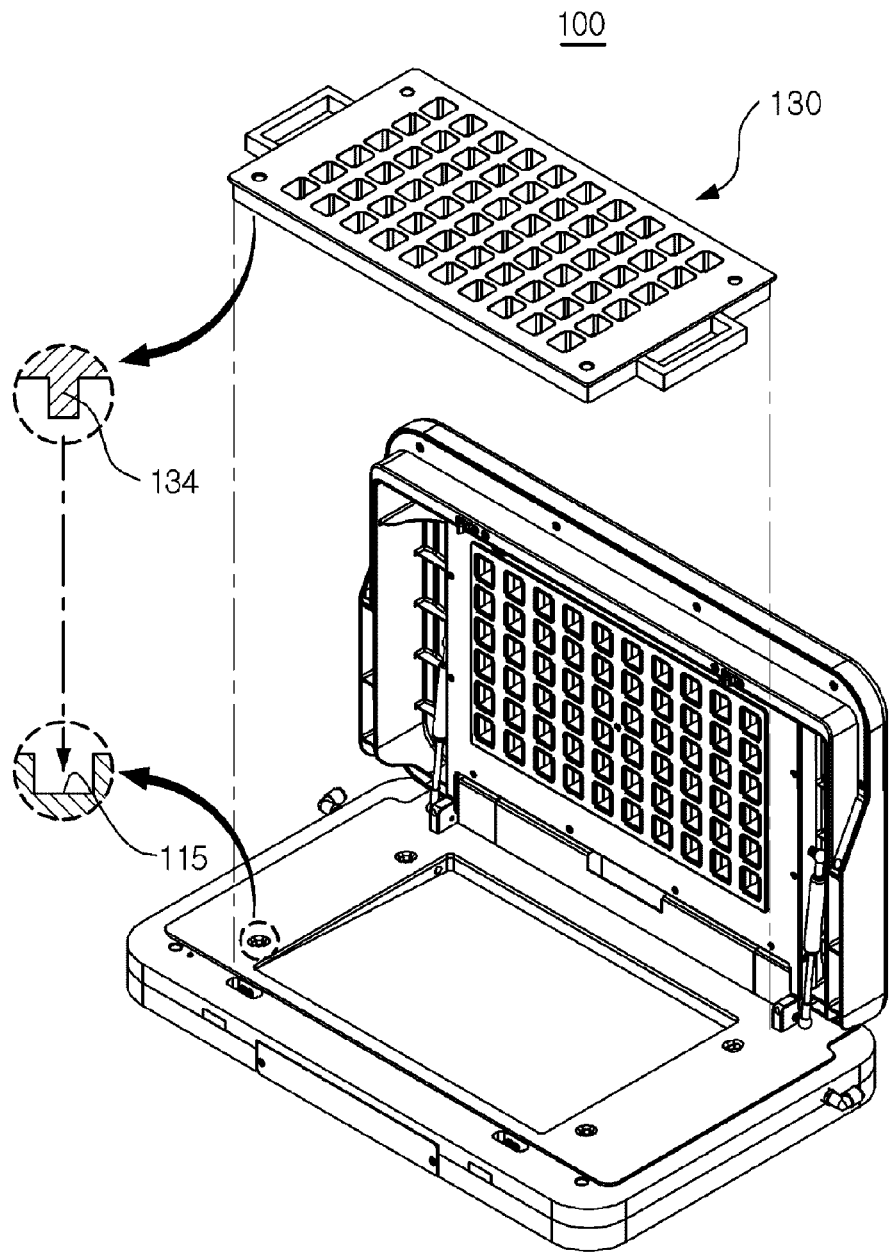
Figure 16:
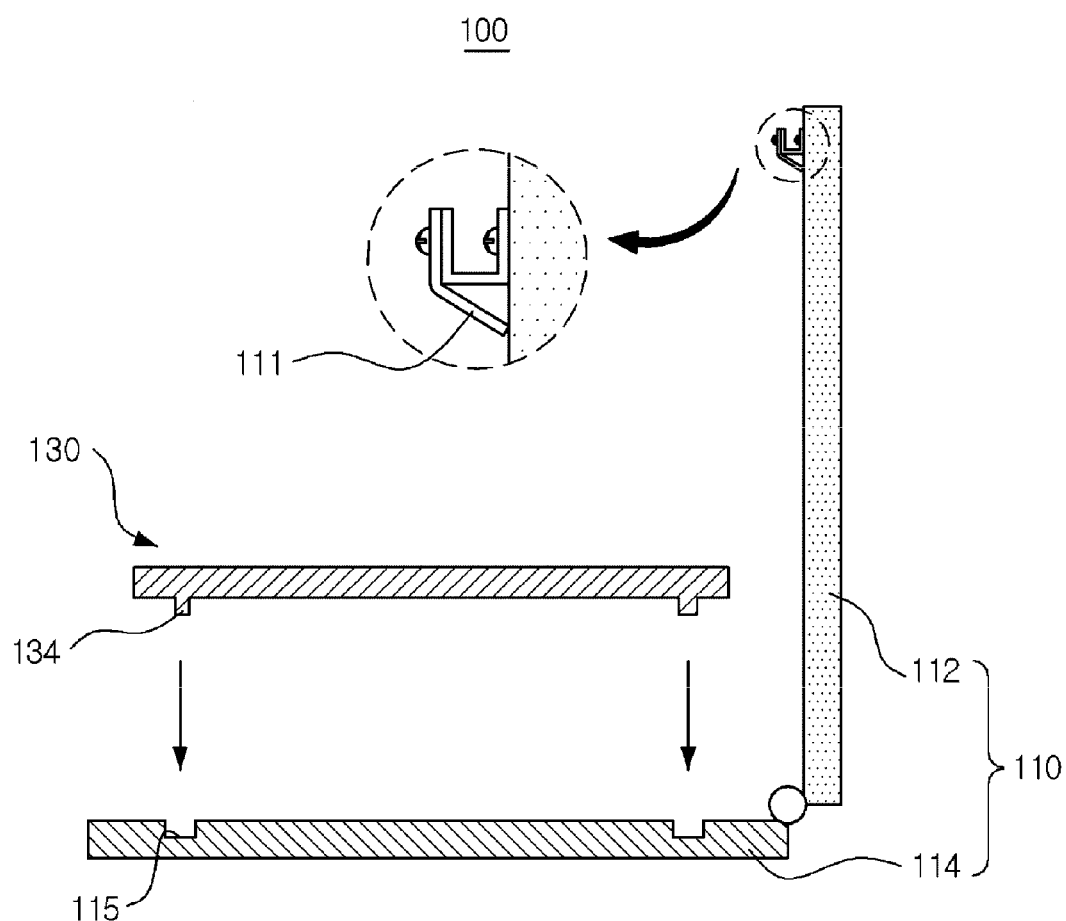

FIGS. 14 to 20 are schematic perspective views illustrating a modified example of a coupling relationship between the main body and the tray which, are disposed in the apparatus for dispensing the tablets according to the present invention, i.e., FIG. 14 is a schematic bottom perspective view of the apparatus for dispensing the tablets according to the present invention, FIG. 15 is a schematic exploded perspective view of the apparatus for dispensing the tablets according to the present invention, and FIG. 16 is a schematic view of a state before the tray provided in the apparatus for dispensing the tablets is seated on the main body according to the present invention.

Figure 17:
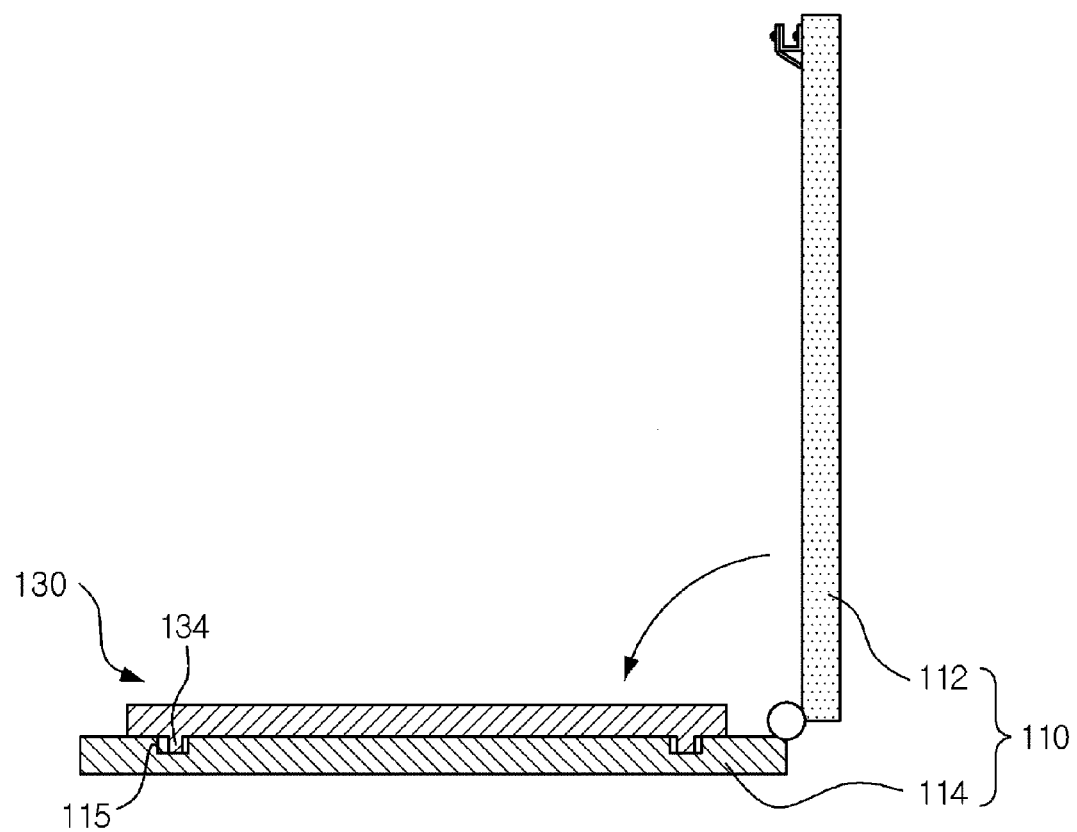
Figure 18:
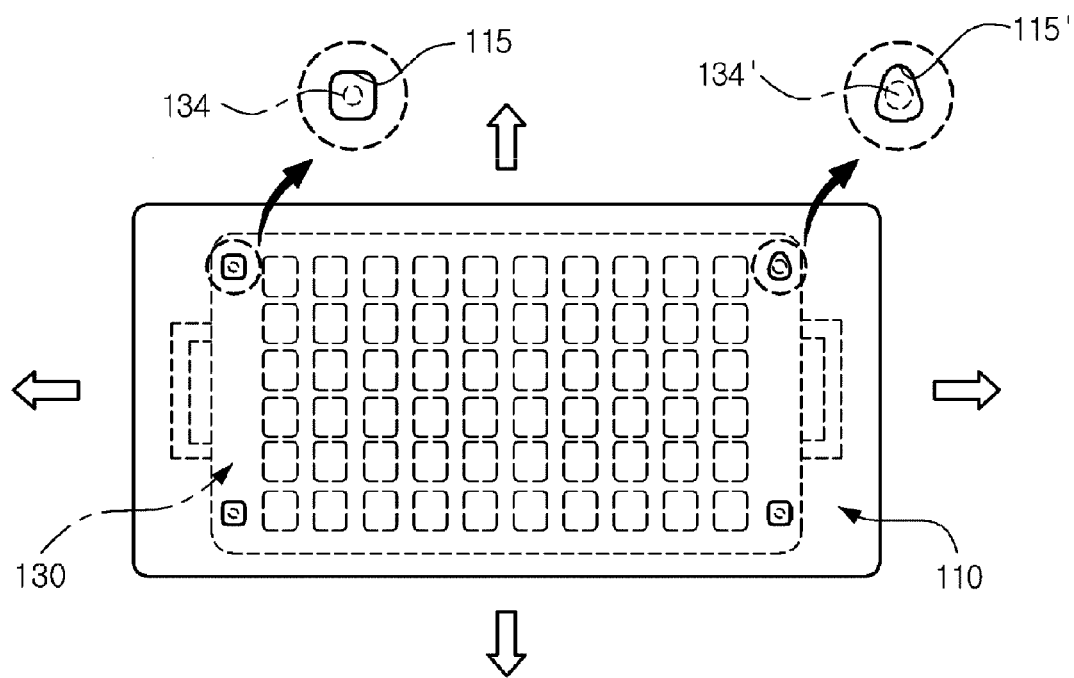
Figure 19:
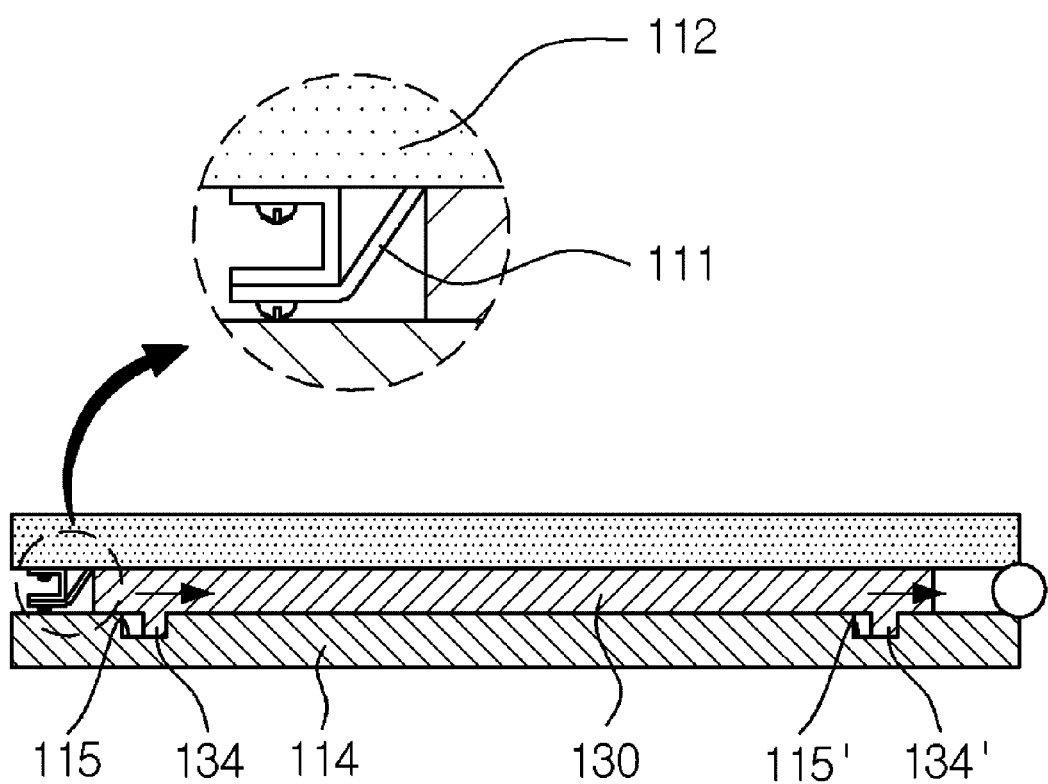
Figure 20:
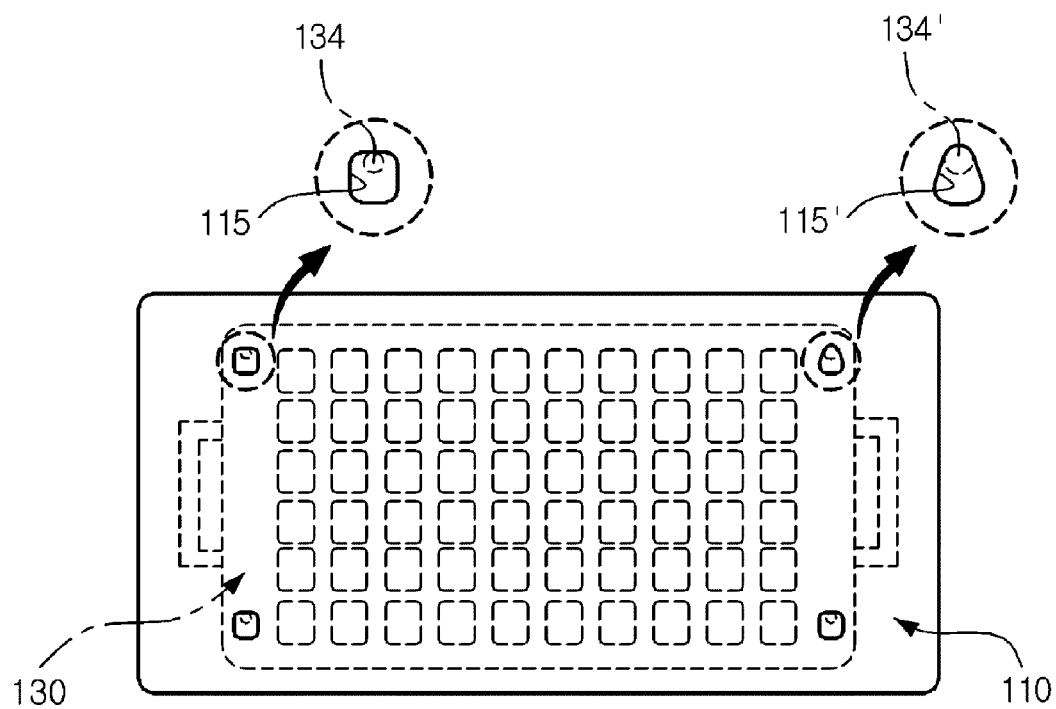

Also, FIGS. 17 and 18 are a schematic view and schematic plan view illustrating a process of seating the tray onto the main body, and FIGS. 19 and 20 are a schematic view and schematic plan view illustrating a process in which the tray is seated on the main body and then fixed to the main body by using a pressing part.

First, the dust dispensing apparatus 100 of FIGS. 14 to 20 may include the foregoing tablet dispensing apparatuses 100 and 200. Thus, for convenience of description, the reference numerals of the dust dispensing apparatus 100 of FIGS. 1 to 7 will be quoted.

Referring to FIGS. 14 to 16, the tray 130 disposed on the support part 114 of the main body 110 may include at least one insertion protrusion 134 that protrudes from the bottom surface of the tray 130. Also, the support part 114 may include at least one insertion groove 115 that is recessed to guide a position of the tray 130.

Here, the insertion groove 115 into which the insertion protrusion 134 is inserted may have a size greater than that of the insertion protrusion 134.

Thus, in the case where the tray 130 is disposed on the support part 114, the user such as the pharmacist may easily insert the insertion protrusion 134 into the insertion groove 115 due to the difference in relative size even though the insertion protrusion 134 is approximately disposed around the insertion groove 115.

Although the insertion protrusion 132 is disposed on the bottom surface of the tray 130, the insertion groove 106 is defined in the support part 104 in FIGS. 11 to 13, the present invention is not limited thereto. For example, the insertion protrusion 132 may be disposed on the support part 104, and the insertion groove 106 may be defined in the bottom surface of the tray 130. However, for convenience of description, the structure in which the insertion groove 106 is defined in the support part 104, and the insertion protrusion 132 is disposed on the bottom surface of the tray 130 will be exemplified.

At least one pressing part 111 for pressing the tray 130 when the cover part 112 is closed may be disposed on the cover part 112 of the main body 110. This will be described later.

Referring to FIGS. 17 and 18, when the tray 130 is disposed on the support part 114, the tray 130 may slightly move on the support part 114 in vertical and horizontal directions due to the difference in relatively size between the insertion groove 115 and the insertion protrusion 134.

Thus, when the cover part 112 is closed, the tray 130 has to be fixed to a predetermined position by being pushed toward one side of the support part 114 due to an external force. This may be realized by the pressing part 111 disposed on the cover part 112.

Referring to FIGS. 19 and 20, the cover part 112 may include at least one pressing part 111 to press the tray 130 that is movably disposed on the support part 114 toward one side of the support part 114.

That is, the pressing part 111 may inclinedly protrude from an inner edge of the cover part 112. Thus, when the cover part 112 is closed, an inclined surface may smoothly push the one edge of the tray 130.

Thus, when the cover part 112 is fully closed, it may prevent the tray 130 from further moving by the pressing force of the pressing part 111. Thus, the tray 130 may be stably fixed.

That is, when the tray 130 is pushed by the pressing part 111, at least one of the insertion protrusions 134 disposed on the tray 130 may be closely attached to a portion of the insertion groove 115 to fix the tray 130.

As a result, the at least one of the insertion grooves 115 may be a fixing groove 115' that is closely attached to at least a portion of an outer surface of an insertion protrusion 134' inserted into at least one of the insertion grooves 115 by the pressing force to fix the tray 130.

Here, the fixing groove 115' may have an approximately triangular shape so that the fixing groove 115' is closely attached to the outer surface of the insertion protrusion 134'.

Here, the fixing groove 115' may be at least one of the insertion groves 115. Here, the insertion protrusion 134' inserted into the fixing groove 115' of the insertion protrusions 134 may have the largest size.

This is done for maximizing easy of the insertion when the tray 130 is initially fixed to the support part 114 by providing the insertion protrusion 134, which is inserted into the insertion groove 115 except for the fixing groove 115', having a relatively small size and also improving the adhesion force with the fixing groove 115' by providing the insertion protrusion 134', which is inserted into the fixing groove 115', having a relatively large size.

Thus, the tray 130 for manually dispensing the tablets may be easily accurately mounted by the insertion protrusions 134 and 134', the insertion groove 115, and the fixing groove 115 so that a non-skilled person may ably use the apparatus.

While the present invention has been particularly shown and described with reference to exemplary embodiments thereof, it will be understood by those of ordinary skill in the art that various changes in form and details may be made therein without departing from the spirit and scope of the present invention as defined by the following claims.

That is, although the tablets are manually inputted into the tablet input parts 113 and 213 by the user such as the pharmacist, the present invention is not limited thereto. For example, the tablets may be automatically inputted by using an automatic device.

Figure 21:
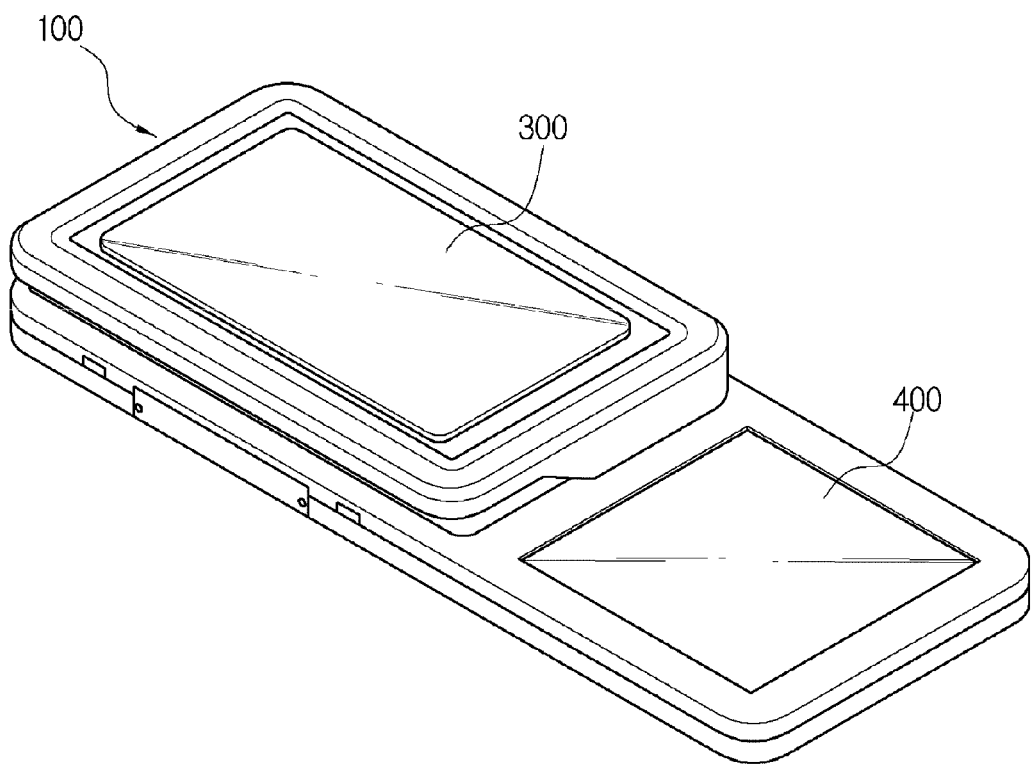
FIG. 21 is a schematic perspective view illustrating a modified example of an outer appearance of the apparatus for dispensing the tablets according to the present invention.

FIG. 21 is a schematic perspective view illustrating a modified example of an outer appearance of the apparatus for dispensing the tablets according to the present invention.

A tablet dispensing apparatus 10*a* including a display unit 400 on one side of the tablet dispensing apparatus 100 or 200 according to the foregoing embodiment illustrated in FIG. 21. The tablet dispensing apparatus 10*a* may include all components and/or features of the tablet dispensing apparatus 100 or 200 according to the foregoing embodiment or include only portions of the components and/or only portions of the features of the tablet dispensing apparatus 100 or 200 according to the foregoing embodiment.

The display unit 400 may display information for operating the tablet dispensing apparatus 10*a*, an operation state of the tablet dispensing apparatus 10*a*, and information that is performed by a processor disposed in the tablet dispensing apparatus 10*a* and/or a processor connected to the tablet dispensing apparatus 10*a* to control the operation of the tablet dispensing apparatus. For example, in the tablet dispensing apparatus 10*a*, an user interface (UI) or graphic user interface (GUI) with respect to tablets that have to be manually dispensed by an operator such as a pharmacist may be displayed on the display unit 400.

The display unit 400 may include at least one of a liquid crystal display, a thin film transistor-liquid crystal display, an organic light-emitting diode, a flexible display, and a 3D display.

A portion of the above-described displays may be provided as a transparent or light-transmissive display so that the inside thereof is seen therethrough. This may be called a transparent display. A representative example of the transparent display may include a transparent LCD. A rear structure of the display unit 400 may also be implemented by utilizing a light transmissive structure. Due to the above structure, the operator may see an object located in the rear side of the display unit 400 through the region occupied by the display unit 400.

At least two display units 400 may be provided according to the implementation method of the tablet dispensing apparatus 10*a*. For example, a plurality of display units may be disposed on a single surface so as to be separated from each other or in the form of a single body. Also, the display units may be disposed on different surfaces from each other.

When the display unit 400 and a sensor (hereinafter, called a "touch sensor") for detecting a touch operation are mutually layered with respect to each other (hereinafter, called a "touch screen"), the display unit 400 may be used as an input unit in addition to the output unit. For example, the touch sensor may be provided as a touch film, a touch sheet, or a touch pad.

The touch sensor may convert a variation in pressure applied to a specific position of the display unit 400 or capacitance generated at the specific position of the display unit 400 into an electrical input signal. The touch sensor may detect a pressure while being touched in addition to a touched position and area.

When the touch sensor detects an touch input, signals corresponding to the touch input may be transmitted into a touch controller. The touch controller may process the signals to transmit data corresponding to the processed signals to the processor. Thus, the tablet dispensing apparatus 10*a* may determine a touched area of the display unit 400.

Figure 22:
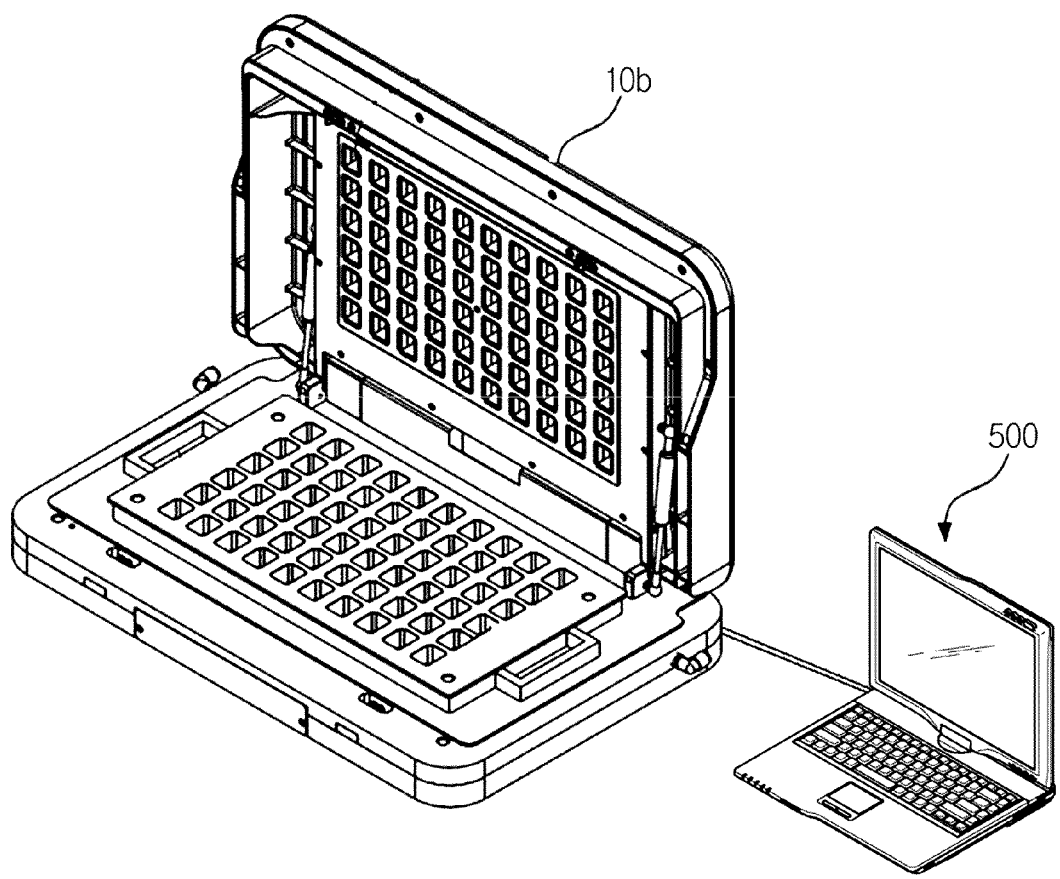
FIG. 22 is a schematic view of a state in which the apparatus for dispensing the tablets is connected to the other electronic equipment according to the present invention.

FIG. 22 is a schematic view of a state in which the apparatus for dispensing the tablets is connected to the other electronic equipment according to the present invention.

Referring to FIG. 22, it is seen that a tablet dispensing apparatus 10b is connected to other electronic equipment. Although the tablet dispensing apparatus 10b is connected to a notebook in FIG. 13, the electronic equipment connected to the tablet dispensing apparatus 10b is not limited to the notebook. For example, the tablet dispensing apparatus 10b may be connected to desktops, tablet PCs, Smartphone, and the like.

Although not shown in detail, each of the tablet dispensing apparatuses 100, 200, and 10a described with reference to FIGS. 1 to 21 may include a processor for controlling an overall operation of the tablet dispensing apparatuses 100, 200, and 10a. However, the tablet dispensing apparatus 10b of FIG. 22 does not include the processor. If the tablet dispensing apparatus 10b itself does not include the processor, the overall operation of the tablet dispensing apparatus 10b may be controlled through a processor provided in the other electronic equipment 500 connected to the tablet dispensing apparatus 10b of FIG. 22.

As illustrated in FIG. 22, when the tablet dispensing apparatus 10b is connected to the other electronic equipment 500, and a display device is provided in the other electronic equipment 500, information for operating the tablet dispensing apparatus 10b, an operation state of the tablet dispensing apparatus 10b, and information processed by the processor may be displayed through the display device. For example, in the tablet dispensing apparatus 10b, an user interface (UI) or graphic user interface (GUI) with respect to tablets that have to be manually dispensed by an operator such as a pharmacist may be displayed on the display device.

Hereinafter, a method for controlling the tablet dispensing apparatus according to the foregoing embodiment of the present invention will be described.

Hereinafter, in the method for controlling the tablet dispensing apparatus, for convenience of description, although a method for controlling the tablet dispensing apparatus 100, 200, 10a, or 10b according to the foregoing embodiment is exemplified, the control method for controlling the tablet dispensing apparatus is not limited to the method for controlling the tablet dispensing apparatus 100, 200, 10a, or 10b.

Also, the above-described display unit may be the display unit 400 disposed in the tablet dispensing apparatus 10a of FIG. 21. However, as illustrated in FIG. 22, when the other electronic equipment 500 is connected to the tablet dispensing apparatus 10b, the display unit may be the display device (a predetermined device for displaying) provided in the other electronic equipment 500.

Further, although not shown in detail in the drawings, each of the tablet dispensing apparatuses 100, 200, 10a, and 10b may include an input unit for receiving predetermined information from a user so as to operate the each of the tablet dispensing apparatuses 100, 200, 10a, and 10b and a communication part for receiving information from other electronic equipment. As described with reference to FIG. 22, when the other electronic equipment 500 is connected to the tablet dispensing apparatus 10b, the tablet dispensing apparatus 10b may receive information from the user or other electronic equipment through an input unit disposed in the other electronic equipment 500 (for example, a keyboard, a touch pad, a touch screen, a mouse, and the like) and a communication part (for example, a wireless communication module and a wired communication module).

Figure 23:
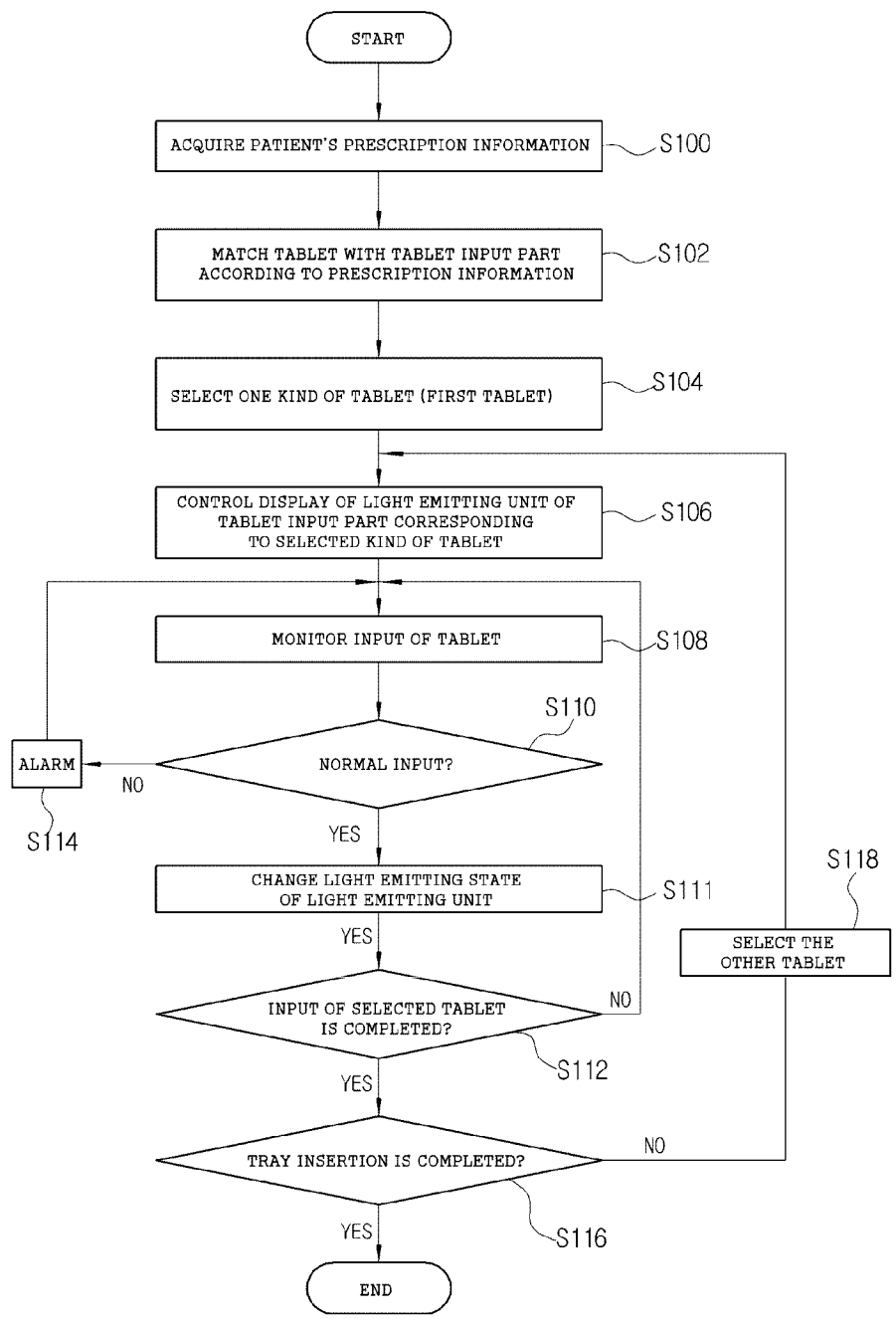
FIG. 23 is a flowchart for explaining a control method of the apparatus for dispensing the tablets according to the present invention.

FIG. 23 is a flowchart for explaining a control method of the apparatus for dispensing the tablets according to the present invention.

First, although the control method described with reference to FIG. 23 may be one of the methods for controlling the tablet dispensing apparatuses 100, 200, 10a, and 10b according to the foregoing embodiment, for convenience of description, the reference numerals of the tablet dispensing apparatus 100 described with reference to FIGS. 1 to 7 will be quoted.

Referring to FIG. 23, a method for controlling a tablet dispensing apparatus 100 according to the present invention may include a process (S100) of acquiring prescription information of a patient, a process (S102) of matching tablets with tablet input parts 113 and 213 according to the prescription information, a process (S104) of selecting one kind of tablet (hereinafter, referred to as a "first tablet") of the tablets to be inputted according to the prescription information, a process (S106) of confirming the tablet input part 113 corresponding to the selected tablet to control a light emitting unit 140 corresponding to the confirmed tablet input part 113, and a process (S108) of monitoring whether the tablet is accurately inputted through the confirmed tablet input part 113 according to the prescription information.

Then, it is determined whether the tablet is accurately normally inputted in operation S110. If the tablet is normally inputted, a process (S111) of changing a light emitting state of the light emitting unit 140 to match the normally inputted state may be performed, and then, a process (S112) of further determining whether the selected tablet is completely inputted may be performed. If the tablet is abnormally inputted, a process (S114) for alarming the abnormal input to allow the abnormal input to be informed to a user such as a pharmacist may be performed through various manners. Also, when the selected tablet is completely inputted, a process (S116) of determining whether tablets are completely dispensed into a tray 130 may be performed. If the selected tablet is not completely dispensed into the tray 130, the process may return to the operation S108 to repeatedly perform the operations S108 to S112. If it is determined that the tablets are completely dispensed into the tray 130 in the operation S116, the method for controlling the tablet dispensing apparatus according to an embodiment of the present invention is finished. On the other hand, if it is determined that the tablets are not completely dispensed into the tray 130, a process (S118) of selecting a second tablet different from the first tablet may be performed. Here, after the second tablet is selected, the process may return to the operation S106 to repeatedly perform the operations S106 to S116.

Hereinafter, each of the processes will be described in more detail.

First, the user such as the pharmacist may locate the tray 130 in an inner space of a main body 110, i.e., an upper side of a collection space S of a support part 114. Here, an insertion protrusion 134 disposed on the tray 130 may be inserted into an insertion groove 115 defined in the support part 114 to stably fix the tray 130 to the support part 114.

Here, whether the tray 130 is accurately inserted into the main body 110 may be sensed. If the tray 130 is not accurately inserted, a predetermined alarm may be outputted. On the other hand, if the tray 130 is accurately inserted, a predetermined process may be performed to acquire prescription information for dispensing the tablets into the tray 130 in operation S100.

The prescription information for dispensing the tablets into the tray 130 may be prescription information that is prescribed for one patient. Alternatively, the prescription information for dispensing the tablets into the tray 130 may be prescription information that is prescribed for two patients.

The prescription information may include kinds of tables to be taken by the patient for one dosage and an amount of tablets that are administered for one dosage. Also, the kinds and amount of tablets that are taken for one dosage may vary according to whenever the patient takes the tablets. The prescription information may include all of the above-described information. FIG. 24 is a view illustrating one example of prescription information obtained from the apparatus for dispensing the tablets according to the present invention. For example, as illustrated in FIG. 24A, kinds and amount (one tablet A, one tablet B, and two tablets C) of tablets to be taken at the morning may be different from kinds and amount (no tablet B, no tablet B, and two tablets C) of tablets to be taken at the lunch and kinds and amount (no tablet A, two tablets B, and two tablets C) of tablets to be taken at the dinner.

The prescription information may include information with respect to how many days do the patient takes the tablets. The kinds and amount of tablets to be tanked for the patient may vary according to the number of days for taking the tablets. The prescription information may also include this information. For example, kinds and amount of tablets to be taken for second and third days as illustrated in FIGS. 24B and 15C may be different from those of tablets to be taken for first day as illustrated in FIG. 24A.

After or just when the prescription information is acquired, each of the kinds and amount of tablets corresponding to the one dosage may match all or at least a portion of the plurality of tablet input parts 113 disposed in the tray 130 in operation S102.

Figure 25:
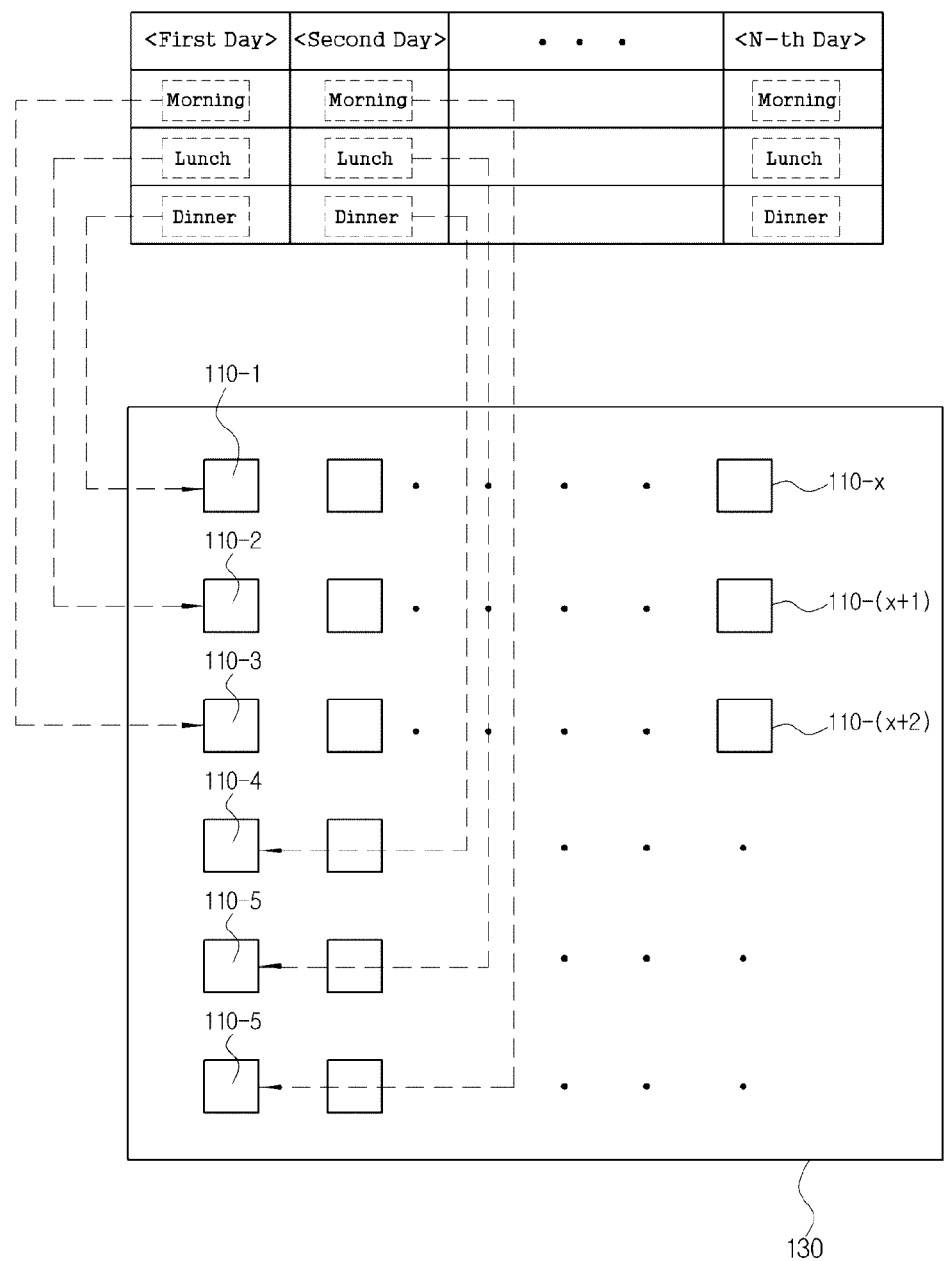
FIG. 25 is a view for explaining a state in which the prescription information and the tablet input part disposed in the tray match each other by the apparatus for dispensing the tablets according to the present invention.

FIG. 25 is a view for explaining a state in which the prescription information and the tablet input part disposed in the tray 130 match each other by the tablet dispensing apparatus according to the present invention. For example, as illustrated in FIG. 25, the tablets to be taken at the morning for the first day may match a first tablet input part 113-1 of the tray 130, the tablets to be taken at the lunch for the first day may match a second tablet input part 113-2 of the tray 130, and the tablets to be taken at the dinner for the first day may match a third tablet input part 113-3 of the tray 130. Similarly, tablets to be taken for the second day to an N-th day may match respective tablet input parts 113.

In the above-described matching state, the first tablet to be dispensed into each of the tablet input part 113 may be selected in operation S104. The tablets to be dispensed may be selected in various manners.

First, the tablet dispensing apparatus 100 may display kinds of tablets to be dispensed on the display unit on the basis of the acquired prescription information. Thus, the user such as the pharmacist may perform an input for selecting tablets to be dispensed, and then select the tablets to be dispensed. For example, when the acquired prescription information is as same as illustrated in FIG. 24, the display unit may display information with respect to the tablets A, B, C, and D. Accordingly, the user such as the pharmacist may select tablets to be dispensed of the displayed tablets. Here, the user may use an input unit such as a keyboard, a mouse, a touch pad, a touch screen, or the like to select the tablets.

Second, in addition to the use of the input unit such as the keyboard, the mouse, the touch pad, the touch screen, or the like for selecting the tablets by the user, a bar cord displayed on packages of the tablets or an RFID tag provided on the packages of the tablets may be used to select the tablets. For example, to select the tablet A, the user may allow a bar cord reader provided in the tablet dispensing apparatus 100 to recognize the bar cord displayed on the package of the prepared tablet A, thereby selecting the tablet A. In case where the RFID tag is used, a predetermined tablet may be selected similar to the case in which the bar cord is used. However, in the case where the RFID tag is used, the RFID reader has to be provided in the tablet dispensing apparatus 100.

Third, the tablet dispensing apparatus 100 may randomly select one tablet without user's selection on the basis of the acquired prescription information.

However, plural kinds of tablets to be dispensed will be described as an example. In the result confirmed on the basis of the prescription information, if one kind of tablets to be dispensed is used, a unique kind of tablets may be selected regardless of the user's selection.

As described above, when one tablet is selected of the plurality of tablets to be dispensed, the tablet input part 113 into which the selected first tablet is inputted may be confirmed on the basis of the information matching through the operation S102. In operation S106, a light emitting state of the light emitting unit corresponding to the confirmed tablet input part 113 may be controlled.

The light emitting state of the light emitting unit 140 corresponding to the confirmed tablet input part 113 into which the first tablet has to be inputted among all of the tablet input parts 113 provided in the tray 130 may be controlled different from light emitting states of the light emitting units 140 corresponding to the rest tablet input parts 113. Thus, the tablet input part into which the first tablet selected by the user has to be inputted and the rest tablet input parts may be visually instinctively distinguished. Hereinafter, for convenience of description, the tablet input part into which the first tablet has to be inputted may be particularly called a "first tablet input part".

Figure 26:
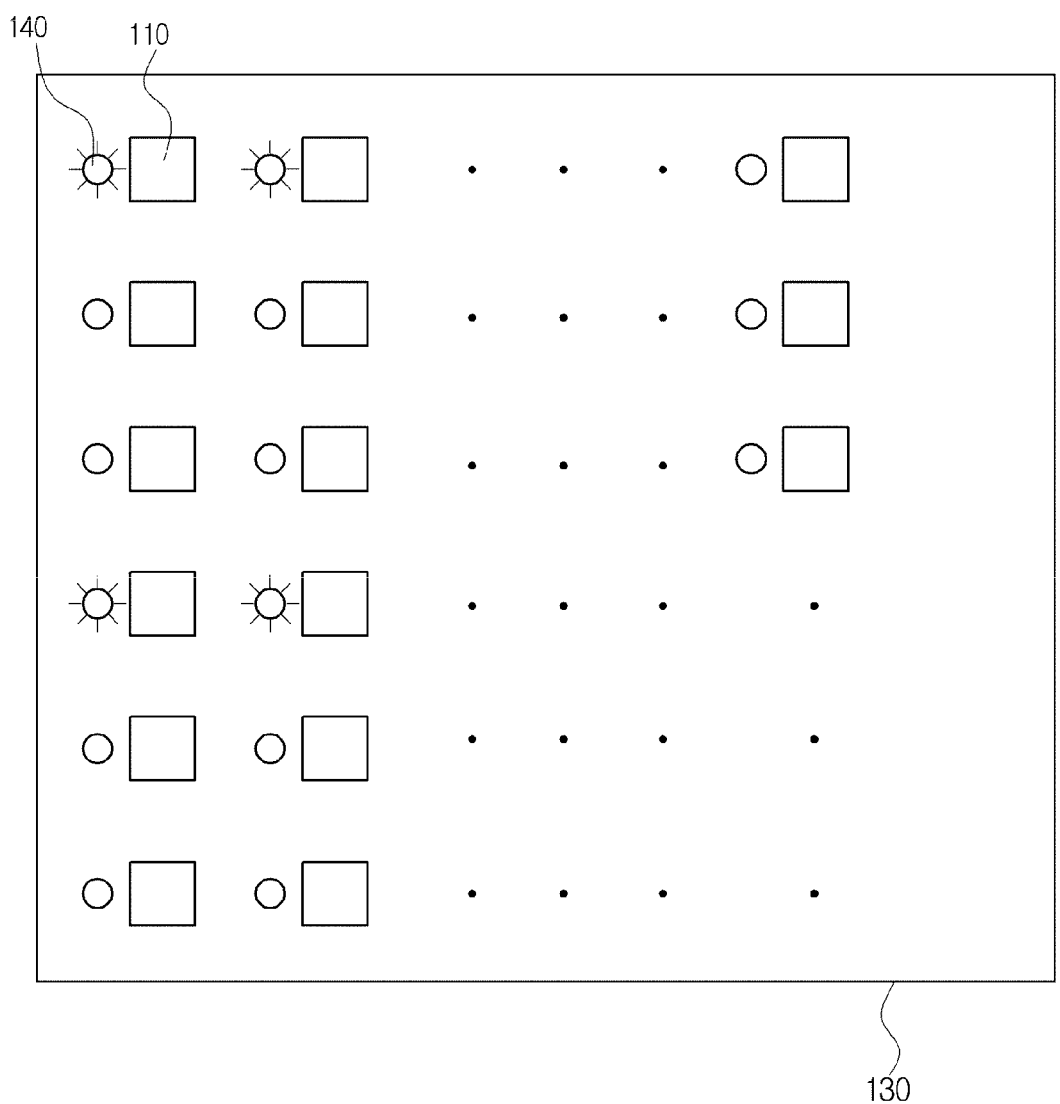
FIG. 26 is a view for explaining an example of a method for controlling a light emitting unit corresponding to the tablet input part by using the apparatus for dispensing the tablets according to the present invention.

FIG. 26 is a view for explaining an example of a method for controlling a light emitting unit corresponding to the tablet input part by using the apparatus for dispensing the tablets according to the present invention. For example, as illustrated in FIG. 26, only the light emitting unit 140 corresponding to the first tablet input part may be turned on, and the light emitting units 140 corresponding to the rest tablet input parts 113 may be turned off.

For another example, all of the light emitting units 140 corresponding to all of the tablet input parts 113 provided in the tray 130 may be turned on, and the light emitting unit 140 corresponding to the first tablet input part may have brightness different from those of the light emitting units 140 corresponding to the rest tablet input parts. That is, the light emitting unit 140 corresponding to the first tablet input part may have relatively bright brightness.

For another example, the light emitting unit 140 corresponding to the first tablet input part may be controlled so that the light emitting unit 140 is turned on/off with a relatively short period, and the light emitting units 140 corresponding to the rest tablet input parts may be controlled so that the light emitting units 140 are continuously turned on. That is, the light emitting unit 140 may be controlled so that only the light emitting unit 140 corresponding to the first tablet input part is flickered.

For another example, the light emitting unit 140 corresponding to the first tablet input part may be controlled so that the light emitting unit 140 having a color A is turned on, and the light emitting units 140 corresponding to the rest tablet input parts may be controlled so that the light emitting units 140 each of which has a color B are turned on.

In addition, a light emitting state of the light emitting unit 140 corresponding to the first tablet input part and a light emitting state of each of the light emitting units 140 corresponding to the rest tablet input parts may be controlled to be different from each other.

The light emitting states of the light emitting units 140 corresponding to the tablet input parts 113 may be controlled to be different from each other according to an amount of tablets to be administrated. That is, even though the same tablet has to be inputted, a light emitting state of the light emitting unit corresponding to the tablet input part 113 into which one corresponding tablet has to be inputted and a light emitting state of the light emitting unit 140 corresponding to the tablet input part 113 into which two corresponding tablets have to be inputted may be different from each other.

For example, the light emitting unit 140 corresponding to the tablet input part 113 into which one tablet has to be inputted may be turned on with brightness A, and the light emitting unit 140 corresponding to the tablet input part 113 into which two tablets have to be inputted may be turned on with brightness B. Of cause, if three, four, . . . , n tablets have to be inputted, each of the light emitting units 140 corresponding to the tablet input parts 113 may be turned on with brightness to correspond to the number of tablets.

For another example, the light emitting units 140 may be flickered so that the light emitting unit 140 corresponding to the tablet input part 113 into which one tablet has to be inputted has a flickering period x, and the light emitting unit 140 corresponding to the tablet input part 113 into which two tablets have to be inputted has a flickering period y. Of cause, if three, four, . . . , n tablets have to be inputted, each of the light emitting units 140 corresponding to the tablet input parts 113 may be flickered to correspond to the number of tablets.

Figure 27:
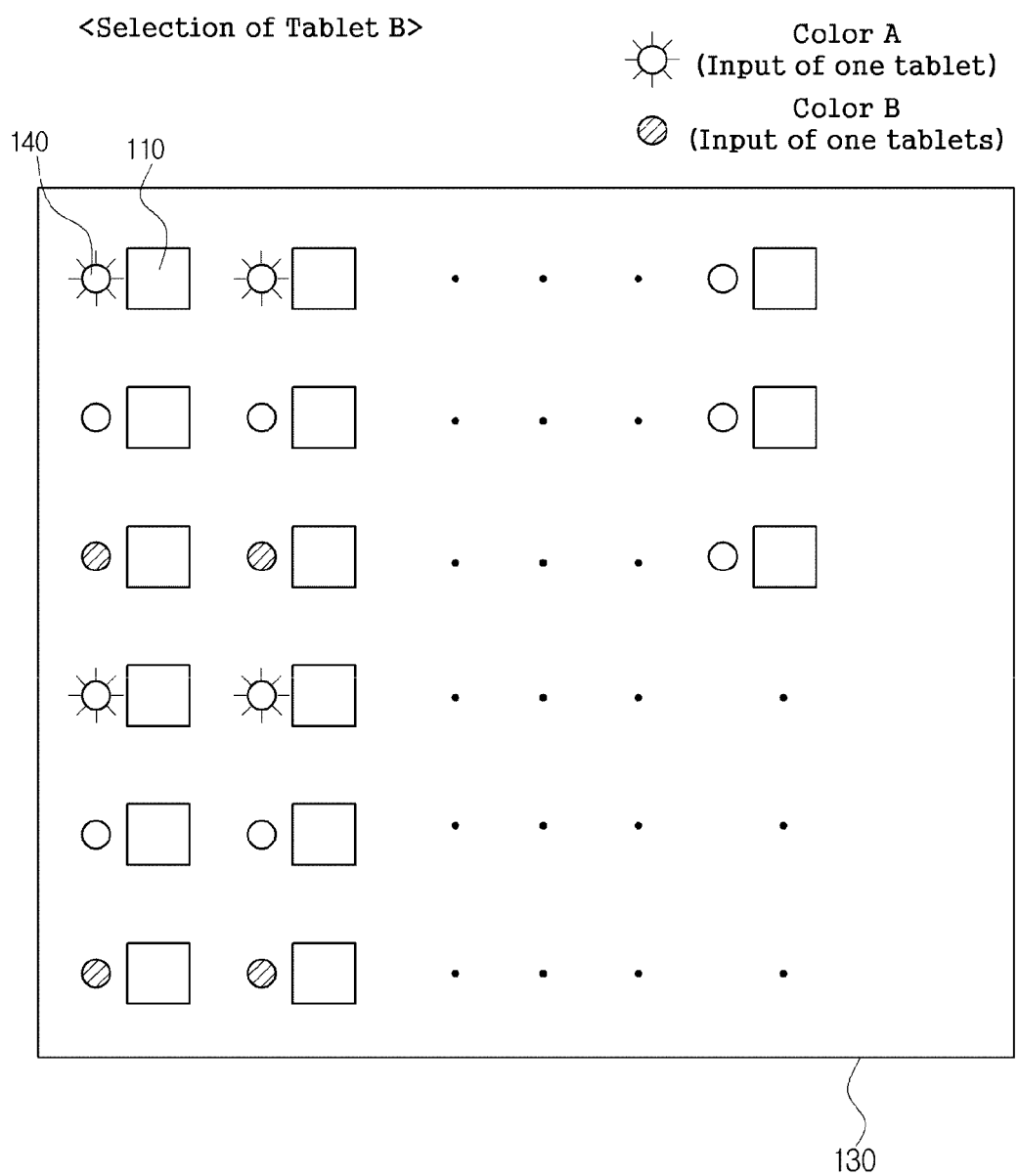
FIG. 27 is a view for explaining another example of the method for controlling the light emitting unit corresponding to the tablet input part by using the apparatus for dispensing the tablets according to the present invention.

For another example, FIG. 27 is a view for explaining another example of the method for controlling the light emitting unit corresponding to the tablet input part by using the apparatus for dispensing the tablets according to the present invention. As illustrated in FIG. 27, the light emitting unit 140 corresponding to the tablet input part 113 into which one tablet has to be inputted may be controlled to be turned on with the color A, and the light emitting unit 140 corresponding to the tablet input part 113 into which two tablets have to be inputted may be controlled to be turned on with the color B. Of cause, if three, four, . . . , n tablets have to be inputted, each of the light emitting units 140 corresponding to the tablet input parts 113 may be tuned on with a color corresponding to the number of tablets.

In addition, the light emitting states of the light emitting units 140 may be variously controlled to be different from each other according to an amount of tablets inputted into each of the tablet input parts.

The light emitting states of the light emitting units 140 corresponding to the tablet input parts 113 may be differently controlled according to the kinds of tablets that have to be inputted. That is, since the light emitting states different from each other correspond to the tablets different from each other, when the kind of tablets that have to be inputted is selected, the light emitting unit 140 may be controlled to allow the light emitting unit 140 to emit light according to the light emitting state corresponding to the selected kind of tablets.

For example, if the kind of tablet to be inputted corresponds to a tablet AA, the light emitting unit 140 corresponding to the tablet input part 113 into which the tablet AA has to be inputted may be turned on with brightness A. If the kind of tablet to be inputted corresponds to a tablet BB, the light emitting unit 140 corresponding to the tablet input part 113 into which the tablet BB has to be inputted may be turned on with brightness B.

For another example, if the kind of tablet to be inputted corresponds to the tablet AA, the light emitting unit 140 corresponding to the tablet input part 113 into which the tablet AA has to be inputted may have a flickering period x. If the kind of tablet to be inputted corresponds to the tablet BB, the light emitting unit 140 corresponding to the tablet input part 113 into which the tablet BB has to be inputted may have a flickering period y.

For example, if the kind of tablet to be inputted corresponds to the tablet AA, the light emitting unit 140 corresponding to the tablet input part 113 into which the tablet AA has to be inputted may be turned on with a color A. If the kind of tablet to be inputted corresponds to a tablet BB, the light emitting unit 140 corresponding to the tablet input part 113 into which the tablet BB has to be inputted may be turned on with a color B.

As described above, when the display of the light emitting unit 140 corresponding to the tablet input part 113 is controlled to visually display the tablet input part 113 into which the selected first tablet has to be inputted so that the user confirms the displayed tablet input part 113, the user such as the pharmacist may input the selected first tablet into the displayed tablet input part 113.

Here, in operation S108, the tablet dispensing apparatus 100 may monitor whether the tablet is accurately inputted into the tablet input part 113.

Through the operation S108, the tablet dispensing apparatus 100 may monitor whether the tablet is inputted into the tablet input part 113 that is confirmed in the operations S100 to S106 and/or whether the accurate number of tablets is inputted. While the monitoring is performed, when the tablet is inputted into the tablet input part 113, the tablet dispensing apparatus 10 may determine whether the tablet is accurately normally inputted in operation S110.

Then, if the tablet is accurately inputted into the tablet input part 113 according to the prescription information, the light emitting state of the light emitting unit 140 may change according to the inputted state of the tablet into the tablet input part 113 in operation S111. The inputted state of the tablet into the tablet input part 113 may be determined on the basis of the result obtained by the sensing of the input sensor 120.

FIG. 28 is a view for explaining an example of changing a light emitting state of the light emitting unit of the apparatus for dispensing the tablets according to the present invention.

Hereinafter, an example of a process of changing a light emitting state of the light emitting unit 140 according to the inputted state of the tablet will be described with reference to FIG. 28. This may be applied to the tablet dispensing apparatuses 100, 200, 10*a*, and 10*b* according to the foregoing embodiment, and thus, for convenience of description, the reference numerals of the tablet dispensing apparatus 100 described with reference to FIGS. 1 to 7 will be quoted.

For example, as illustrated in FIG. 26, when the user such as the pharmacist inputs the tablet into one tablet input part 113 in the state where the light emitting unit 140 corresponding to the tablet input part 113 into which the selected first tablet has to be inputted is turned on, the input sensor 120 may sense the input of the table. Thus, as illustrated in FIG. 28A, the tablet dispensing apparatus 100 may turn off the light emitting unit 140 corresponding to the tablet input part into which the tablet is inputted. Continuously, when the tablet is inputted into the other tablet input part 113, as illustrated in FIG. 28B, the light emitting unit 140 corresponding to the other tablet input part 113 may also be turned off.

FIG. 29 is a view for explaining another example of changing the light emitting state of the light emitting unit of the apparatus for dispensing the tablets according to the present invention.

Hereinafter, another example of a process of changing a light emitting state of the light emitting unit 140 according to the inputted state of the tablet will be described with reference to FIG. 29. This may be applied to the tablet dispensing apparatuses 100, 200, 10a, and 10b according to the foregoing embodiment, and thus, for convenience of description, the reference numerals of the tablet dispensing apparatus 100 described with reference to FIGS. 1 to 7 will be quoted.

For another example, as illustrated in FIG. 27, when one tablet is inputted into the tablet input part 113 into which one selected first tablet has to be inputted as illustrated in FIG. 29 in a state where the light emitting units 140 respectively corresponding to the tablet input part 113 into two selected first tablets have to be inputted and the tablet input part 113 into which one tablet has to be inputted are turned on with colors different from each other, the light emitting unit 140 corresponding to the tablet input part 113 may be turned off. When one tablet is inputted into the tablet input part 113 into which two selected tablets have to be inputted, as illustrated in FIG. 29B, the light emitting unit 140 corresponding to the tablet input part 113 may change from the light emitting color B into the light emitting color A. When an additional tablet is further inputted as illustrated in FIG. 20C into the tablet input part 113 into which only one tablet is inputted although two tablets have to be inputted in the state of FIG. 29B, the light emitting unit 140 corresponding to the tablet input part 113 may be turned off. As described above, in a process of counting the number of tablets that are accurately inputted, the input sensor 120 may additionally include a sensor that is realized by a light emitting device 122 and a light receiving device 124, a pressure sensor for measuring a weight of the tablet inputted into the tablet input part 113, or a vibration sensor for sensing vibration generated when the tablet is inputted into the tablet input part 113. However, it may not be necessary to provide the pressure sensor or the vibration sensor as the input sensor 120 so as to count the number of inputted tablets.

For another example, in the situation in which two tablets have to be inputted into the tablet input part 113, as described above, when one tablet is inputted into the tablet input part 113 into which two tablets have to be inputted, the light emitting unit 140 corresponding to the tablet input part 113 may be continuously maintained to the color B, and then, when two tablets are accurately inputted into the tablet input part 113, the light emitting unit 140 corresponding to the tablet input part 113 may be turned off, instead of unconditionally changing the color of the light emitting unit 140 corresponding to the tablet input part 113 by counting the number of tablets inputted into the tablet input part 113.

In the above-described example in which the light emitting state of the light emitting unit 140 changes according to the inputted state of the tablet into the tablet input part 113, although the process in which the light emitting unit 140 is turned off is described an example, the present invention is not limited thereto. For example, various methods for changing the light emitting state of the light emitting unit 140 may be applied as long as the light emitting unit 140 changes in light emitting state through the method in which the color changes, or the flickering period changes and the method for clearly instinctively informing the input of the tablet into the tablet input part 113 to visually inform the input of the tablet to the user as described above.

In the description with reference to FIG. 29, although the case in which two tablets are continuously inputted into the tablet input part 113 into which two tablets have to be inputted is described as an example, the present invention is not limited thereto. For example, after one tablet is inputted into the tablet input part 113 into which two tablets have to be inputted, a tablet may be inputted into the other tablet input part 113, and then, one tablet may be additionally inputted into the tablet input part 113 into which two tablets have to be inputted.

Referring again to FIG. 23, in the operation S108 and S110, if it is determined that the tablet is incorrectly inputted into the tablet input part 113, the tablet dispensing apparatus 100 may output an alarm through a predetermined method to the user such as the pharmacist.

If it is determined that the following exemplary situation occurs, the tablet dispensing apparatus 100 may determine that the tablet is incorrectly inputted into the tablet input part 113. However, the situation in which it is determined that the tablet is incorrectly inputted into the tablet input part 113 may include other states in addition to the exemplary situations that will be described below.

First, when N+m tablets (where, m is a real number greater than zero) are inputted into the tablet input part 113 into which N tablets (where, N is a real number) have to be inputted, it may be determined that the tablets are incorrectly inputted. That is, if it is determined that at least two tablets are inputted into the tablet input part 113 into which one tablet has to be inputted, it may be determined that the tablet is incorrectly inputted. Or, if it is determined that at least one tablet is inputted into the tablet input part 113 into which the tablet does not have to be inputted (i.e., in case of N=0), it may be determined that the tablet is incorrectly inputted. Here, it may be unnecessary that N is a natural number. In some cases, an amount of tablets to be inputted may be a rear number of about 0.5.

Second, when N-m tablets (where, m is a real number greater than N and less than zero) are inputted into the tablet input part 113 into which N tablets (where, N is a real number greater than zero) have to be inputted, it may be determined that the tablets are incorrectly inputted if the m tablets are not additionally inputted within a preset time. That is, if one tablet is not additionally inputted within a preset time (for example, one minute) after one tablet is inputted into the tablet input part into which two tablets have to be inputted, it may be determined that the tablet is incorrectly inputted. The preset time may be determined by various manners. However, since this description unnecessarily obscures subject matters of the present invention, its detailed description will be omitted.

If it is determined that the tablet is incorrectly inputted in the operation S108 and/or operation S110 according to the above-described situations, an alarm may be outputted. Here, the alarm may be outputted in various manners.

For example, the light emitting unit 140 may be controlled so that the light emitting state of the light emitting unit 140 corresponding to the tablet input part 113 into which the tablet is incorrectly inputted is differently displayed when compared to that of the other light emitting unit 140. That is, the light emitting unit 140 corresponding to the tablet input part 113 into which the tablet is incorrectly inputted may be flickered.

For another example, when the tablet is incorrectly inputted into the tablet input part 113, all of the light emitting units 140 corresponding to the plurality of tablet input parts 113 may be turned on for a predetermined time to inform the incorrect input of the tablet to the user. Then, only the light emitting unit 140 corresponding to the tablet input part into which the tablet is incorrectly inputted may be controlled to be turned on.

For another example, a message for informing the incorrect input of the tablet to the user may be visually outputted through the display unit. Here, to allow the user to more easily inform the incorrect input of the tablet into any tablet input part 113, the tablet input part 113 into which the tablet is incorrectly inputted may be displayed on an image obtained by visualizing and outputting the plurality of tablet input parts 113 provided in the tray 130 so that the tablet input part 113 into which the tablet is incorrectly inputted is distinguished.

For another example, the message for informing the incorrect input of the tablet may be outputted to the user by using a sound. Here, what position the tablet input part 113 into which the tablet is incorrectly inputted is disposed may be informed to the user by using the sound.

Then, as described above, the tablet dispensing apparatus 100 may monitor whether the first tablets selected in the operation S104 are normally inputted. Here, in operation S112, it may be determined whether the first tablets are normally inputted into all of the tablet input parts 113 into which the selected first tablets have to be inputted.

In the result determined in the operation S112, if it is determined that all of the selected first tablets are not normally inputted into the tablet input part 113, the process may return to the operation S108, and then, the tablet dispensing apparatus 100 may repeatedly perform the operations S108 to S114.

On the other hand, in the result determined in the operation S112, if it is determined that all of the selected first tablets are normally inputted into the tablet input part 113, it may be determined whether all kinds of tablets included in the prescription information obtained in the operation S100 are completely dispensed in operation S116. That is, when the prescription information as illustrated in FIG. 24 is acquired, it may be determined whether the tablets A, B, C, and D are completely dispensed as described above.

In the result determined in the operation S116, when it is determined that the tablets are completely dispensed, the tablet dispensing apparatus 100 may inform the complete dispensing of the tablets to the user through the alarm, and then, the tablet dispensing process may be finished.

On the other hand, in the result determined in the operation S116, when it is determined that the dispensing of the tablet is not finished, the tablet dispensing apparatus 100 may select a second tablet different from the first tablet selected in the operation S104 in operation S118. That is, when the prescription information as illustrated in FIG. 15 is acquired, the tablet A may be firstly selected, and the dispensing of the tablet A may be finished when the input of the tablet into the tablet input part 110 starts. However, when it is determined that the dispensing of the tablets B, C, and D is not finished, the tablet dispensing apparatus 100 may determine that the input of all of the tablets into the tray is not finished. Here, since a method for selecting the second tablet is similar to that for selecting the first tablet, its detailed description will be omitted.

As described above, according to the tablet dispensing apparatus according to an embodiment of the present invention, the manual dispensing of the tablet T into the tray 130 by the user such as the pharmacist may be instinctively induced.

Thus, in the operation for dispensing the tablets into the tray 130 by the user such as the pharmacist, efficiency may be more improved, and also, accuracy may be improved.

Hereinafter, the method for controlling the tablet dispensing apparatus according to an embodiment of the present invention has been described.

In the description with respect to the method for controlling the tablet dispensing apparatus according to an embodiment of the present invention, as illustrated in FIGS. 26 to 29, the light emitting unit 140 corresponding to each of the tablet input parts 113 may be realized by using one light emitting device. However, it may be unnecessary that the light emitting unit 140 is realized by one light emitting device. For example, the light emitting unit 140 may be realized by using at least two light emitting devices. For example, the light emitting unit 140 may be realized by using at least two LED devices.

Further, as illustrated in FIGS. 26 to 29, for convenience of description, although illustrated as if the light emitting unit 140 is provided in the tray 130, the light emitting unit 140 may be provided in the main body 110 as illustrated in FIGS. 1 to 7.

Also, it is unnecessary to provide the light emitting unit 140 corresponding to one tablet input part 113 as one light emitting unit 140. For example, a plurality of light emitting units 140 adjacent to the tablet input part 113 may correspond to one tablet input part 113. That is, from the point of view of one light emitting unit 140, it may be unnecessary that one light emitting unit 140 corresponds to one tablet input part 113. For example, the one light emitting unit 140 may correspond to at least two tablet input parts 113. For example, as illustrated in FIGS. 26 to 29, when one tablet input part 113 is selected, only the light emitting unit 140 that is disposed at a left side of the selected tablet input part 113 may correspond to the tablet input part 113. Alternatively, when one tablet input part 113 is selected, all of the light emitting unit 140 that is disposed at a right side of the selected tablet input part 113 as well as the light emitting unit 140 that is disposed at the left side of the selected tablet input part 113 may be turned on.

In the above-described tablet dispensing apparatus according to the present invention, the components described in the embodiments may not be necessary. Thus, the components may be included or omitted adequate fro the objects of the tablet dispensing apparatus.

Also, in the method for controlling the tablet dispensing apparatus according to the present invention, the processes in each of the embodiments are not necessary, and thus, the above-described processes in each of the embodiments may be selectively performed. Also, it is unnecessary to perform the processes according to each of the embodiments in foregoing order. For example, the process that is described later may be performed first than the process that is described first.

Also, in the method for controlling the tablet dispensing apparatus according to the present invention, the embodiments may be individually or combinedly used. Furthermore, the embodiments may be individually realized or combined with each other. Also, the processes according to each of the embodiments and the processes according to another embodiment may be individually realized or combined with each other.

Also, the method for controlling the tablet dispensing apparatus according to the present invention may be stored in a computer-readable recording medium in a code or program form.

The present invention has been described above with reference to the aforementioned embodiments. It is evident, however, that many alternative modifications and variations will be apparent to those having skill in the art in light of the foregoing description. Accordingly, the present invention embraces all such alternative modifications and variations as fall within the spirit and scope of the appended claims. Also, the embodiments set forth therein is not so limitedly, but all or part of the embodiments can be selectively combined so as to derive many variations.

The invention claimed is:

1. A method for controlling an apparatus for dispensing tablets, the method comprising:
    acquiring information with respect to the tablets to be inputted into at least a portion of a plurality of tablet input parts provided in a tray;
    controlling a plurality of light emitting units corresponding to the plurality of tablet input parts on the basis of the acquired information; and
    changing light emitting states of the plurality of light emitting units on the basis of the result obtained by sensing of a plurality of input sensors for sensing whether the tablets are inputted into the plurality of tablet input parts,
    wherein the plurality of tablet input parts include at least a first tablet input part and a second tablet input part,
    wherein the plurality of input sensors include a first input sensor and a second input sensor corresponding to the first tablet input part and the second tablet input part, respectively, and
    wherein the changing light emitting states comprises changing a light emitting state of the light emitting unit according to the first tablet input part on the basis of a result obtained by sensing of the first input sensor each time the first input sensor senses that one tablet is inputted into the first tablet input part when the tablets inputted into the first tablet input part are two or more.

2. The method of claim 1, further comprising:
    selecting one of a plurality of kinds of tablets when the kinds of tablets to be inputted are provided in plurality; and
    confirming at least one tablet input part, into which the selected kind of tablets has to be inputted, of the plurality of tablet input parts.

3. The method of claim 2, wherein the controlling of the light emitting units comprises controlling a light emitting state of the light emitting unit corresponding to the confirmed at least one tablet input part.

4. The method of claim 3, wherein the controlling of the light emitting units comprises controlling the plurality of light emitting units so that the light emitting state of the light emitting unit corresponding to the confirmed at least one tablet input part is different from those of the remaining light emitting units except for the confirmed at least one tablet input part of the plurality of tablet input parts.

5. The method of claim 1, wherein the controlling of the light emitting units comprises:
    acquiring an input amount of tablets to be inputted into the second tablet input part from the information with respect to the tablets to be inputted; and
    controlling a light emitting state of the light emitting unit corresponding to the second tablet input part according to the input amount of tablets.

6. The method of claim 1, further comprising:
    counting an input number of tablets to be inputted into the second tablet input part; and
    changing a light emitting state of the light emitting unit corresponding to the second tablet input part according to the input number of tablets.

* * * * *